US009228169B2

(12) United States Patent
Schlenoff et al.

(10) Patent No.: US 9,228,169 B2
(45) Date of Patent: Jan. 5, 2016

(54) THIN FILMS FOR CONTROLLED CELL GROWTH

(71) Applicant: Florida State University Research Foundation, Inc., Tallahassee, FL (US)

(72) Inventors: Joseph B. Schlenoff, Tallahassee, FL (US); David S. Salloum, Blue Ash, OH (US); Thomas C. Keller, III, Tallahassee, FL (US); Scott G. Olenych, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 14/741,062

(22) Filed: Jun. 16, 2015

(65) Prior Publication Data

US 2015/0284680 A1 Oct. 8, 2015

Related U.S. Application Data

(62) Division of application No. 11/130,972, filed on May 17, 2005, now Pat. No. 9,056,125.

(60) Provisional application No. 60/571,818, filed on May 17, 2004.

(51) Int. Cl.
| | | |
|---|---|---|
| *A61K 31/00* | (2006.01) | |
| *C12N 5/00* | (2006.01) | |
| *A61K 31/785* | (2006.01) | |
| *A61L 27/26* | (2006.01) | |
| *A61L 27/34* | (2006.01) | |
| *A61L 27/54* | (2006.01) | |
| *A61L 29/08* | (2006.01) | |
| *A61L 29/16* | (2006.01) | |
| *A61L 31/10* | (2006.01) | |
| *A61K 31/16* | (2006.01) | |

(52) U.S. Cl.
CPC .............. *C12N 5/0068* (2013.01); *A61K 31/16* (2013.01); *A61K 31/785* (2013.01); *A61L 27/26* (2013.01); *A61L 27/34* (2013.01); *A61L 27/54* (2013.01); *A61L 29/085* (2013.01); *A61L 29/16* (2013.01); *A61L 31/10* (2013.01); *A61L 2300/424* (2013.01); *A61L 2400/18* (2013.01); *A61L 2420/06* (2013.01); *A61L 2430/00* (2013.01); *A61L 2430/12* (2013.01); *A61L 2430/16* (2013.01); *C12N 2537/00* (2013.01)

(58) Field of Classification Search
None
See application file for complete search history.

(56) References Cited

U.S. PATENT DOCUMENTS

| | | |
|---|---|---|
| 3,467,604 A | 9/1969 | Michaels |
| 4,169,023 A | 9/1979 | Sata et al. |
| 4,289,600 A | 9/1981 | Lazarz et al. |
| 4,497,720 A | 2/1985 | Moriga et al. |
| 4,501,835 A | 2/1985 | Berke |
| 4,554,076 A | 11/1985 | Speaker |
| 4,654,235 A | 3/1987 | Effenberger et al. |
| 4,863,823 A | 9/1989 | Hiro et al. |
| 4,920,021 A | 4/1990 | Kimura et al. |
| 5,208,111 A | 5/1993 | Decher et al. |
| 5,312,710 A | 5/1994 | Tomita et al. |
| 5,380,644 A | 1/1995 | Yonkoski et al. |
| 5,711,915 A | 1/1998 | Siegmund et al. |
| 5,807,636 A | 9/1998 | Sheu et al. |
| 5,939,323 A | 8/1999 | Valentini et al. |
| 6,355,300 B1 | 3/2002 | Stirniman et al. |
| 6,402,918 B1 | 6/2002 | Schlenoff et al. |
| 6,468,657 B1 | 10/2002 | Hou et al. |
| 6,610,789 B2 | 8/2003 | Watakabe et al. |
| 6,670,309 B2 | 12/2003 | Chiba et al. |
| 6,797,444 B2 | 9/2004 | Itami |
| 6,841,054 B2 | 1/2005 | Schlenoff et al. |
| 7,018,709 B2 | 3/2006 | Stevenson et al. |
| 7,094,464 B2 | 8/2006 | Mao et al. |
| 7,223,327 B2 | 5/2007 | Schlenoff et al. |
| 7,238,536 B1 | 7/2007 | Schlenoff et al. |
| 7,713,629 B2 * | 5/2010 | Schlenoff ...................... 428/421 |
| 7,722,752 B2 | 5/2010 | Schlenoff et al. |
| 8,481,017 B2 | 7/2013 | Schlenoff et al. |
| 9,056,125 B2 | 6/2015 | Schlenoff et al. |
| 2002/0053514 A1 | 5/2002 | Locascio et al. |
| 2002/0130045 A1 | 9/2002 | Schlenoff et al. |
| 2003/0078388 A1 | 4/2003 | Basey et al. |
| 2003/0124368 A1 | 7/2003 | Lynn et al. |
| 2003/0215626 A1 | 11/2003 | Hiller et al. |
| 2004/0022691 A1 | 2/2004 | Allen et al. |

(Continued)

OTHER PUBLICATIONS

Mamedov, A. A., et al., "Free-Standing Layer-by-Layer Assembled Films of Magnetite Nanoparticles," Langmuir, 2000, pp. 5530-5533, vol. 16, No. 13.

(Continued)

*Primary Examiner* — Hasan Ahmed

(74) *Attorney, Agent, or Firm* — Senniger Powers LLP

(57) ABSTRACT

A method for controlling the attachment and growth of cells on a surface of an article, the method comprising contacting the article with living tissue, living organisms, or with water in an aqueous system comprising living organisms wherein the article comprises a substratum having a surface and a film on the surface, the film comprising a network of a net positively charged composition and a net negatively charged composition, wherein the net positively charged composition comprises a net positively charged polyelectrolyte or the net negatively charged composition comprises a net negatively charged polyelectrolyte, and the net positively charged polyelectrolyte or the net negatively charged polyelectrolyte contain (i) a polymer repeat unit having at least two fluorine atoms, or (ii) a polymer repeat unit having a zwitterion group.

17 Claims, 6 Drawing Sheets

(56) References Cited

U.S. PATENT DOCUMENTS

| | | |
|---|---|---|
| 2004/0044100 A1 | 3/2004 | Schlenoff et al. |
| 2004/0060481 A1 | 4/2004 | Schlenoff |
| 2004/0084312 A1 | 5/2004 | Warner et al. |
| 2004/0149572 A1 | 8/2004 | Schlenoff et al. |
| 2004/0191504 A1 | 9/2004 | Stevenson et al. |
| 2004/0265603 A1 | 12/2004 | Schlenoff |
| 2005/0025675 A1 | 2/2005 | Schlenoff et al. |
| 2005/0287111 A1 | 12/2005 | Schlenoff et al. |

OTHER PUBLICATIONS

Mendelsohn, J. D., et al., "Fabrication of Microporous Thin Films from Polyelectrolyte Multilayers," Langmuir, 2000, pp. 5017-5023, vol. 16, No. 11.

Mendelsohn, J. D., et al., "Rational Design of Cytophilic and Cytophobic Polyelectrolyte Multilayer Thin Films," Biomacromolecules, 2003, pp. 96-106, vol. 4, No. 1.

Michaels, A. S., "Polyelectrolyte Complexes," Industrial & Engineering Chemistry, Sep. 24, 1965, pp. 32-40, vol. 57, No. 10.

Mohwald, H., et al., "Chapter 13—Smart Capsules," Multilayer Thin Films, 2002, pp. 363-392.

Mrksich, M., et al., "Surface Plasmon Resonance Permits in Situ Measurement of Protein Absorption on Self-Assembled Monolayers of Alkanethiolates on Gold," Langmuir, 1995, pp. 4383-4385, vol. 11, No. 11.

Muller, M., et al., "Deposition and Bioadhesion Properties of Polymer Multilayers: An in-situ-ATR-FTIR-Study," Macromolecular Symposia, 1999, pp. 149-159, vol. 145.

Muller, M., et al., "Deposition and Properties of Polyelectrolyte Multilayers Studied by ATR-FTIR Spectroscopy," Materials Science and Engineering, 1999, pp. 163-169, vol. C 8-9.

Muller, M., et al., "Polyelectrolyte Complex Layers: A Promising Concept for Anti-Fouling Coatings Verified by in-situ ATR-FTIR Spectroscopy," Macromolecular Rapid Communications, 1999, pp. 607-611, vol. 20, No. 12.

Muller, M., et al., "Selective Interaction Between Proteins and the Outermost Surface of Polyelectrolyte Multilayers: Influence of the Polyanion Type, pH and Salt," Macromolecular Rapid Communications, 2001, pp. 390-395, vol. 22, No. 6.

Onda, M., et al., "Sequential Actions of Glucose Oxidase and Peroxidase in Molecular Films Assembled by Layer-by-Layer Alternate Absorption," Biotechnology and Bioengineering, Jul. 20, 1996, pp. 163-167, vol. 51, No. 2.

Oner, D., et al., "Ultrahydrophobic Surfaces. Effects of Topography Length Scales on Wettability," Langmuir, 2000, pp. 7777-7782, vol. 16, No. 20.

Ostuni, E., et al., "Self-Assembled Monolayers That Resist the Absorption of Proteins and the Adhesion of Bacterial and Mammalian Cells," Langmuir, 2001, pp. 6336-6343, vol. 17, No. 20.

Overberger, C.G. et al., "Imidazole-Containing Polymers. Synthesis and Polymerization of the Monomer 4(5)-Vinylimidazole," Journal of the American Chemical Society, Apr. 5, 1963, pp. 951-955, vol. 85.

Philipp, B., et al., "Polyelectrolyte Complexes—Recent Developments and Open Problems," Progress in Polymer Science, An International Review Journal, 1989, pp. 91-172, vol. 14.

Petrak, K., "Biocompatible Particles Based on Block-Copolymer Aggregates for Intravascular Administration," Journal of Bioactive and Compatible Polymers, Apr. 1993, pp. 178-187, vol. 8, No. 2.

Richert, L., et al., "Cell Interactions with Polyelectrolyte Multilayer Films," Biomacromolecules, 2002, pp. 1170-1178, vol. 3, No. 6.

Richert, L., et al., "Improvement of Stability and Cell Adhesion Properties of Polyelectrolyte Multilayer Films by Chemical Cross-Linking," Biomacromolecules, 2004, pp. 284-294, vol. 5, No. 2.

Richert, L., et al., "Layer by Layer Buildup of Polysaccharide Films: Physical Chemistry and Cellular Adhesion Aspects," Langmuir, 2004, pp. 448-458, vol. 20, No. 2.

Rosidian, A., et al., "Ionic Self-Assembly of Ultrahard ZrO.sub.2Polymer Nanocomposite Thin Films," Advanced Materials, 1998, pp. 1087-1091, vol. 10, No. 14.

Salloum, D. S., et al., "Protein Absorption Modalities on Polyelectrolyte Multilayers," Biomacromolecules, 2004, pp. 1089-1096, vol. 5, No. 3.

Saltzman, W. M., "Chapter 19—Cell Interactions with Polymers," Principles of Tissue Engineering Second Edition, 2000, pp. 221-235, Academic Press.

Schlenoff, J. B., et al., "Sprayed Polyelectrolyte Multilayers," Langmuir, 2000, pp. 9968-9969, vol. 16, No. 26.

Schwinte, P., et al., "Stabilizing Effects of Various Polyelectrolyte Multilayer Films on the Structure of AbsorbedEmbedded Fibrinogen Molecules: An ATR-FTIR Study," J. Phys. Chem. B, 2001, pp. 11906-11916, vol. 105, No. 47.

Serizawa, T., et al., "Alternating Bioactivity of Polymeric Layer-by-Layer Assemblies: Anticoagulation vs. Procoagulation of Human Blood," Biomacromolecules, 2002, pp. 724-731, vol. 3, No. 4.

Stepp, J., et al., "Electrochromism and Electrocatalysis in Viologen Polyelectrolyte Multilayers," Journal of the Electrochemical Society, Jun. 1997, pp. L155-L157, vol. 144, No. 6.

Stroeve, P., et al., "Gas Transfer in Supported Films Made by Molecular Self-Assembly of Ionic Polymers," Thin Solid Films 284-285, 1996, pp. 708-712.

Sukhishvili, S. A., et al., "Layered, Erasable Polymer Multilayers Formed by Hydrogen-Bonded Sequential Self-Assembly," Macromolecules, 2002, pp. 301-310, vol. 35, No. 1.

Szleifer, I., "Polymers and Proteins: Interactions at Interfaces," Biomaterials, 1997, pp. 337-344. Takayama, S., et al., "Chapter 18—Patterning of Cells and Their Environment," Principles of Tissue Engineering Second Edition, 2000, pp. 209-220, Academic Press.

Tamada, Y., et al., "Fibroblast Growth on Polymer Surfaces and Biosynthesis of Collagen," Journal of Biomedical Materials Research, Jul. 1994, pp. 783-789, vol. 28, No. 7.

Thierry, B., et al., "Bioactive Coatings of Endovascular Stents Based on Polyelectrolyte Multilayers," Biomacromolecules, 2003, pp. 1564-1571, vol. 4, No. 6.

Thomson, R. C., et al., "Chapter 21—Polymer Scaffold Processing," Principles of Tissue Engineering Second Edition, 2000, pp. 251-262, Academic Press.

Tieke, B., et al., "Ultrathin Self-Assembled Polyelectrolyte Multilayer Membranes," The European Physical Journal E, 2001, pp. 29-39, vol. 5.

Tryoen-Toth, P., et al., "Viability, Adhesion, and Bone Phenotype of Osteoblast-like Cells on Polyelectrolyte Multilayer Films," 2002, pp. 657-667.

Tsuchida, E., et al., Advances in Polymer Science, vol. 45.

Worth, N. F., et al., "Vascular Smooth Muscle Cell Phenotypic Modulation in Culture is Associated With Reorganisation of Contractile and Cytoskeletal Proteins," Cell Motility and the Cytoskeleton, 2001, pp. 130-145, vol. 49.

Yoo, D., et al., "Controlling Bilayer Composition and Surface Wettability of Sequentially Absorbed Multilayers of Weak Polyelectrolytes," Macromolecules, 1998, pp. 4309-4318, vol. 31, No. 13.

Zou, H., et al., "Monolithic Stationary Phases for Liquid Chromatography and Capillary Electrochromatography," Journal of Chromatography A, 2002, pp. 5-32, vol. 954.

Cheng, Y., et al., "Ultrathin Polypeptide Multilayer Films for the Fabrication of Model Liquidliquid Electrochemical Interfaces," J. Phys. Chem. B 1999, pp. 8726-8731, vol. 103, No. 41, Published Sep. 18, 1999.

Atala, A., et al., Synthetic Biodegradable Polymer Scaffolds, 1997, Birkhauser, Boston, MA.

Barker, S. L. R., et al., "Control of Flow Direction in Microfluidic Devices with Polyelectrolyte Multilayers," Anal. Chem., Dec. 15, 2000, pp. 5925-5929, vol. 72, No. 24.

Berg, M. C., et al., "Controlling Mammalian Cell Interactions on Patterned Polyelectrolyte Multilayer Surfaces," Langmuir, 2004, pp. 1362-1368, vol. 20, No. 4.

Boura, C., et al., "Endothelial Cells Grown on Thin Polyelectrolyte Multilayered Films: An Evaluation of a New Versatile Surface Modification," Biomaterials, 2003, pp. 3521-3530, vol. 24.

Caruso, F., et al., "Assembly of Alternating Polyelectrolyte and Protein Multilayer Films for Immunosensing," Langmuir, 1997, pp. 3427-3433, vol. 13, No. 13.

(56) References Cited

OTHER PUBLICATIONS

Caruso, F., et al., "Chapter 12—Coated Colloids: Preparation, Characterization, Assembly and Utilization," Multilayer Thin Films, 2003, pp. 331-362.

Chen, W., et al., "Layer-by-Layer Deposition: A Tool for Polymer Surface Modification," Macromolecules, 1997, pp. 78-86, vol. 30, No. 1.

Chluba, J., et al., "Peptide Hormone Covalently Bound to Polyelectrolytes and Embedded into Multilayer Architectures Conserving Full Biological Activity," Biomacromolecules, 2001, pp. 800-805, vol. 2, No. 3.

Dai, J., et al., "Controlling the Permeability of Multilayered Polyelectrolyte Films Through Derivatization, Cross-Linking, and Hydrolysis," Langmuir, 2001, pp. 931-937, vol. 17, No. 3.

Decher, G., "Fuzzy Nanoassemblies: Toward Layered Polymeric Multicomposites," Science, Aug. 29, 1997, pp. 1232-1237, vol. 277.

Decher, G., "Chapter 1—Polyelectrolyte Multilayers, An Overview," Multilayer Thin Films, 2002, pp. 1-46.

Deyoung, J. P., et al., "Chapter 13—Synthesis of Fluoropolymers in Liquid and Supercritical Carbon Dioxide Solvent Systems," Fluoropolymers 1, 1999, pp. 191-205.

Dubas, S. T., et al., "Swelling and Smoothing of Polyelectrolyte Multilayers by Salt," Langmuir, 2001, pp. 7725-7727, vol. 17, No. 25.

Durstock, M. F., et al., "Dielectric Properties of Polyelectrolyte Multilayers," Langmuir, 2001, pp. 7865-7872, vol. 17, No. 25.

Elbert, D. L., et al., "Thin Polymer Layers Formed by Polyelectrolyte Multilayer Techniques on Biological Surfaces," Langmuir, 1999, pp. 5355-5362, vol. 15, No. 16.

Farhat, T. R., et al., "Doping-Controlled Ion Diffusion in Polyelectrolyte Multilayers: Mass Transport in Reluctant Exchangers," Journal of the American Chemical Society Articles, 2003, pp. 4627-4636, vol. 125, No. 15.

Farhat, T. R., et al., "Ion Transport and Equilibria in Polyelectrolyte Multilayers," Langmuir, 2001, pp. 1184-1192, vol. 17, No. 4.

Fou, A. C., et al., "Fabrication and Properties of Light-Emitting Diodes Based on Self-Assembled Multilayers of Poly (phenylene vinylene)," J. Appl. Phys., May 15, 1996, pp. 7501-7509, vol. 79, No. 10.

Good, R. J., "Contact Angle, Wetting, and Adhesion: A Critical Review," Journal of Adhesion Science and Technology, 1992, pp. 1269-1302, vol. 6, No. 12.

Graul, T. W., et al., "Capillaries Modified by Polyelectrolyte Multilayers for Electrophoretic Separations," Anal. Chem., Sep. 15, 1999, pp. 4007-4013, vol. 71, No. 18.

Halayko, A. J., et al., "Plasticity in Skeletal, Cardiac, and Smooth Muscle Invited Review: Molecular Mechanisms of Phenotypic Plasticity in Smooth Muscle Cells," J. Appl. Physiol., 2001, pp. 358-368, vol. 90.

Hammond, P. T., et al., "Formation of Polymer Microstructures by Selective Deposition of Polyion Multilayers Using Patterned Self-Assembled Monolayers as a Template," Macromolecules, 1995, pp. 7569-7571, vol. 28, No. 22.

Han, D. K., et al., "Absorption Behavior of Fibrinogen to Sulfonated Polyethyleneoxide-Grafted Polyurethane Surfaces," Journal of Biomaterials SciencePolymer Edition, 1993, pp. 401-413, vol. 4, No. 5.

Harris, J. J., et al., "Electrochemical and in Situ Ellipsometric Investigation of the Permeability and Stability of Layered Polyelectrolyte Films," Langmuir, 2000, pp. 2006-2013, vol. 16, No. 4.

Harris, J. J., et al., "Layered Polyelectrolyte Films as Selective, Ultrathin Barriers for Anion Transport," Chem. Mater., 2000, pp. 1941-1946, vol. 12, No. 7.

Harris, J. J., et al., "Synthesis of Passivating, Nylon-Like Coatings through Cross-Linking of Ultrathin Polyelectrolyte Films," J. Am. Chem. Soc., 1999, pp. 1978-1979, vol. 121, No. 9.

Hiller, J. A., et al., "Reversibly Erasable Nanporous Anti-Reflection Coatings from Polyelectrolyte Multilayers," Nature Materials, Sep. 2002, pp. 59-63, vol. 1.

Holmlin, R. E., et al., "Zwitterionic SAMs that Resist Nonspecific Absorption of Protein from Aqueous Buffer," Langmuir, 2001, pp. 2841-2850, vol. 17, No. 9.

Hsieh, M. C., et al., "Surface "Priming" for Layer-by-Layer Deposition: Polyelectrolyte Multilayer Formation on Allylamine Plasma-Modified Poly(tetrafluoroethylene)," Macromolecules, 1997, pp. 8453-8458, vol. 30, No. 26.

Huck, W. T. S., et al., "Patterned Polymer Multilayers as Etch Resists," Langmuir, 1999, pp. 6862-6867, vol. 15, No. 20.

Hyde, F. W., et al., "Comparison of Fluorinated Polymers Against Stainless Steel, Glass and Polypropylene in Microbial Biofilm Adherence and Removal," Journal of Industrial Microbiology & Biotechnology, 1997, pp. 142-149, vol. 19.

Ichinose, I., et al., "Electrostatic Absorption of Cytochrome c on Ultrathin $ZrO_2$-Gel Layers and Preparation of Alternate Multilayers," Langmuir, 2003, pp. 3883-3888, vol. 19, No. 9.

Indolfi, C., et al., "Molecular Mechanisms of In-Stent Restenosis and Approach to Therapy with Eluting Stents," TCM, 2003, pp. 142-148, vol. 13, No. 4.

Ito, Y., et al., "Micropatterned Immobilization of Epidermal Growth Factor to Regulate Cell Function," Bioconjugate Chem., 1998, pp. 277-282, vol. 9, No. 2.

Jessel, N., et al., "Bioactive Coatings Based on a Polyelectrolyte Multilayer Architecture Functionalized by Embedded Proteins," Advanced Materials, May 2, 2003, pp. 692-695, vol. 15, No. 9.

Jiang, X., et al., "Selective Deposition in Layer-by-Layer Assembly: Functional Graft Copolymers as Molecular Templates," Langmuir, 2000, pp. 8501-8509, vol. 16, No. 22.

Jorgenson, J. W., et al., "Zone Electrophoresis in Open-Tubular Glass Capillaries," Analytical Chemistry, Jul. 1981, pp. 1298-1302, vol. 53, No. 8.

Knight, A. W., et al., "Occurrence, Mechanisms and Analytical Applications of Electrogenerated Chemiluminescence," Analyst, May 1994, pp. 879-890, vol. 119.

Kozlovskaya, V., et al., "Hydrogen-Bonded Polymer Capsules Formed by Layer-by-Layer Self-Assembly," Macromolecules, 2003, pp. 8590-8592, vol. 36, No. 23.

Krasemann, L., et al., "Selective Ion Transport Across Self-Assembled Alternating Multilayers of Cationic and Anionic Polyelectrolytes," Langmuir, 2000, pp. 287-290, vol. 16, No. 2.

Ladam, G., et al., "Protein Absorption onto Auto-Assembled Polyelectrolyte Films," Langmuir, 2001, pp. 878-882, vol. 17, No. 3.

Ladam, G., et al., "Protein Interactions with Polyelectrolyte Multilayers: Interactions Between Human Serum Albumin and Polystyrene SulfonatePolyallylamine Multilayers," Biomacromolecules, 2000, pp. 674-687, vol. 1, No. 4.

Lahav, M., et al., "Tailored Chemosensors for Chloroaromatic Acids Using Molecular Imprinted $TiO_2$ Thin Films on Ion-Sensitive Field-Effect Transistors," Analytical Chemistry, Feb. 1, 2001, pp. 720-723, vol. 73, No. 3.

Laurent, D., et al., "Multilayer Assemblies of Redox Polyelectrolytes," Langmuir, 1997, pp. 1552-1557, vol. 13, No. 6.

Levasalmi, J-M., et al., "Poly(4-methyl-1-pentene)-Supported Polyelectrolyte Multilayer Films: Preparation and Gas Permeability," Macromolecules, 1997, pp. 1752-1757, vol. 30, No. 6.

Levenberg, S., et al., "Embryonic Stem Cells in Tissue Engineering," Handbook of Embryonic Stem Cells, pp. 1-29.

Losche, M., et al., "Detailed Structure of Molecularly Thin Polyelectrolyte Multilayer Films on Solid Substrates as Revealed by Neutron Reflectometry," Macromolecules, 1998, pp. 8893-8906, vol. 31, No. 25.

Lvov, Y., et al., "Assembly of Multicomponent Protein Films by Means of Electrostatic Layer-by-Layer Absorption," J. Am. Chem. Soc., 1995, pp. 6117-6123, vol. 117, No. 22.

Lvov, Y., et al., "Biocolloids with Ordered Urease Multilayer Shells as Enzymatic Reactors," Analytical Chemistry, Sep. 1, 2001, pp. 4212-4217, vol. 73, No. 17.

Lvov, Y. M., et al., "Direct Electrochemistry of Myoglobin and Cytochrom $P450_{cam}$ in Alternate Layer-by-Layer Films with DNA and Other Polyions," J. Am. Chem. Soc., 1998, pp. 4073-4080, vol. 120, No. 17.

\* cited by examiner

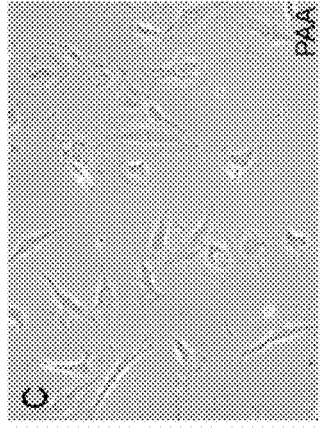
FIG. 4A  FIG. 4B  FIG. 4C
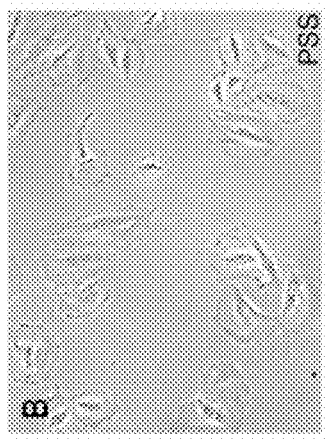
FIG. 4D  FIG. 4E  FIG. 4F
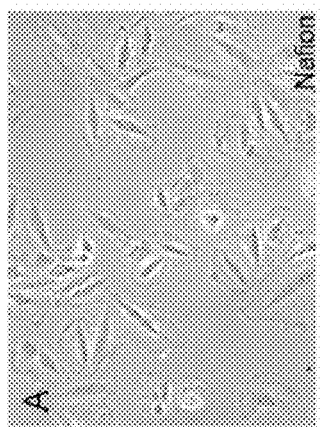
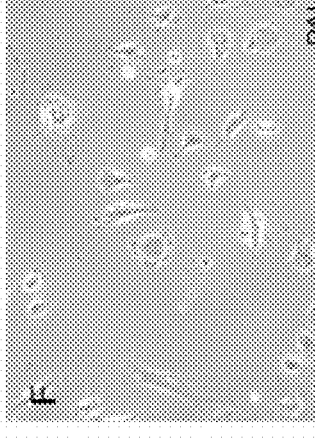
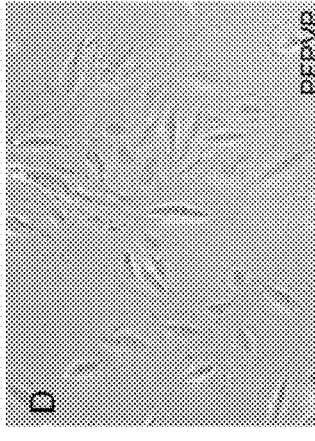

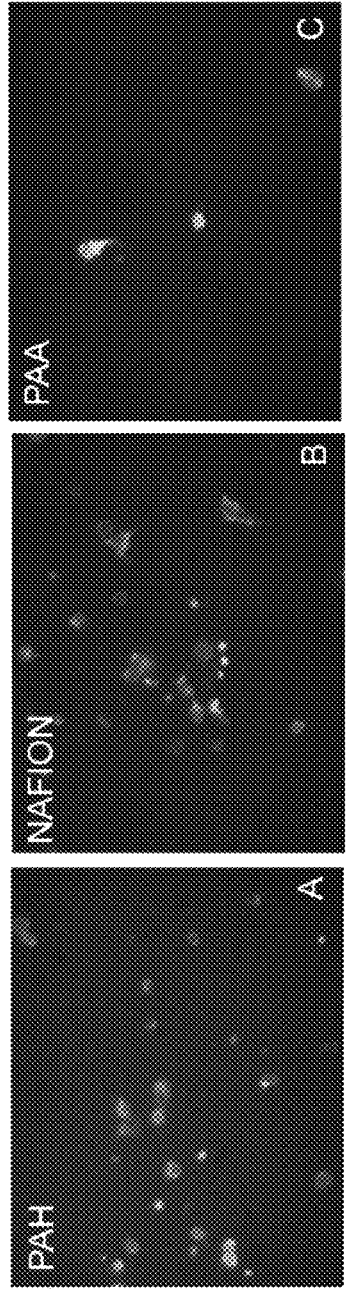
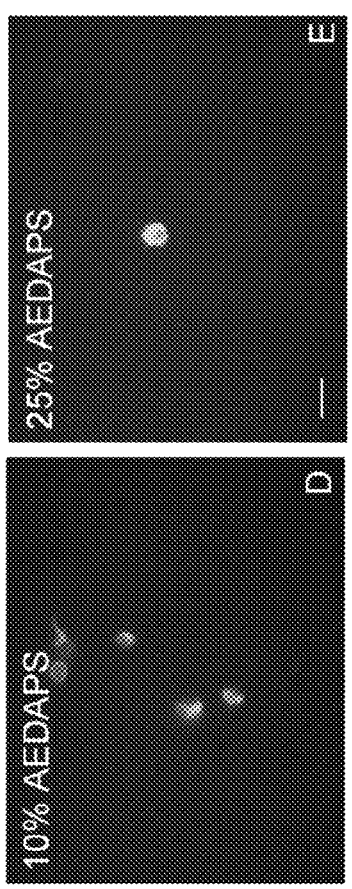
FIG. 9A  FIG. 9B  FIG. 9C  FIG. 9D  FIG. 9E

THIN FILMS FOR CONTROLLED CELL GROWTH

CROSS-REFERENCE TO RELATED APPLICATIONS

This application is a division of U.S. patent application Ser. No. 11/130,972, filed May 17, 2005, issued Jun. 16, 2015 as U.S. Pat. No. 9,056,125, which claims priority from U.S. provisional application Ser. No. 60/571,818, filed on May 17, 2004, the contents of which are incorporated by reference in their entirety.

STATEMENT REGARDING FEDERALLY SPONSORED RESEARCH OR DEVELOPMENT

This invention was made with Government support under Grant DMR 9727717 awarded by the National Science Foundation. The Government has certain rights in this invention.

BACKGROUND OF THE INVENTION

This invention relates generally to the field of cell growth and, more particularly, to using polyelectrolyte complex films to coat surfaces to enhance or inhibit cell growth, adhesion, and differentiation.

In order for cells to adhere and grow on a substrate, the interface between the substrate and the cell growth medium must possess an appropriate combination of physical and chemical properties. Control over the surface of substrate provides for control over cell adhesion. Advantageous properties imparted by a surface range from the complete rejection of any cell adhesion or growth, to cell adhesion without growth, to cell adhesion, growth, and differentiation. The property desired depends on the end-use of the substrate. For example, articles implanted in vivo, such as stents, catheters, and artificial organs, preferably do not induce biochemical processes that lead to scarring and/or rejection of said article. These implants may be advantageously coated with thin films that render them biocompatible. Alternatively, some applications, especially those in tissue engineering, require substrates that encourage the growth, differentiation, and proliferation of cells. A strategy for modifying the cell adhesion and cell growth properties of surfaces is needed.

Polyelectrolytes are macromolecules comprising a plurality of charged repeat units. Amorphous complexes may be formed by contacting solutions of polyelectrolytes bearing opposite charges. The driving force for association, or complexation, of polyelectrolytes is multiple ion pairing between oppositely charged repeat units on different molecules.

Recently, thin films of polyelectrolyte complexes have been prepared using polyelectrolytes which are alternately deposited on a substrate or substratum. See Decher and Schlenoff, Eds., *Multilayer Thin Films-Sequential Assembly of Nanocomposite Materials*, Wiley-VCH, Weinheim (2003); Decher, Science, 277, 1232 (1997). Decher and Hong (U.S. Pat. No. 5,208,111) disclose a method for a buildup of multilayers by alternating dipping, i.e., cycling a substrate between two reservoirs containing aqueous solutions of polyelectrolytes of opposite charge, with an optional rinse step in polymer-free solution following each immersion. Each cycle adds a layer of polymer via ion pairing forces to the oppositely-charged surface and reverses the surface charge thereby priming the film for the addition of the next layer. Films prepared in this manner tend to be uniform, follow the contours and irregularities of the substrate, and are typically between about 10 nm and about 10,000 nm thick. The thickness of a film depends on many factors, including the number of layers deposited, the ionic strength of the solutions, the types of polymers, the deposition time, the solution pH, the temperature, and the solvent used. Although studies have shown that substantial interpenetration of the individual polymer layers results in little composition variation over the thickness of a film, such polymer thin films are, nevertheless, referred to as polyelectrolyte multilayers (PEMUs).

Surface modification using polyelectrolyte multilayers to develop biocompatible materials has been attracting attention lately due to the ease of synthesis and cost-effectiveness of the layer-by-layer technique. See Decher, G., Schlenoff, J. B. *Multilayer Thin Films-Sequential Assembly of Nanocomposite Materials*; Wiley-VCH: Weinheim, Germany, 2003. Surface properties ranging from hydrophobic to hydrophilic, charged to uncharged, and smooth to rough can be generated using a variety of parameters including the chemical nature of the polyelectrolytes and the pH, ionic strength, and temperature used for multilayer synthesis. Because proteins play an important role in the adhesion, spreading, and growth of cells, considerable effort has been expended in developing polyelectrolyte thin films with properties that make the surface adhesive or resistant to protein adsorption. See Muller, M.; Rieser, T.; Kothe, M.; Kessler, B.; Brissova, M.; Lunkwitz, K. *Macromol. Symp.* 1999, 145, 149, Muller, M.; Brissova, M.; Rieser, T.; Powers, A. C.; Lunkwitz, K. Mat. Sci. Eng. C-Bio. S. 1999, 8-9, 163, Muller, M.; Rieser, T.; Lunkwitz, K.; Meier-Haack, J. *Macromol. Rapid. Comm.* 1999, 20, 607, Ladam, G.; Gergely, C.; Senger, B.; Decher, G.; Voegel, J. C.; Schaaf, P.; Cuisinier, F. J. G. *Biomacromolecules* 2000, 1, 674, Ladam, G.; Schaaf, P.; Cuisinier, F. J. G.; Decher, G.; Voegel, J. C. *Langmuir* 2001, 17, 878, and Salloum, D. S.; Schlenoff, J. B. *Biomacromolecules* 2004. Although an understanding of PEMU-protein adsorption is necessary to intelligently engineer cell-biomaterial interaction, it is difficult to predict PEMU-cell biocompatibility from simple measurements of protein adsorption. See Han, D. K.; Ryu, G. H.; Park, K. D.; Jeong, S. Y.; Kim, Y. H.; Min, B. G. *Journal of Biomaterials Science-Polymer Edition* 1993, 4, 401, Ostuni, E.; Chapman, R. G.; Liang, M. N.; Meluleni, G.; Pier, G.; Ingber, D. E.; Whitesides, G. M. *Langmuir* 2001, 17, 6336, and Mendelsohn, J. D.; Yang, S. Y.; Hiller, J.; Hochbaum, A. I.; Rubner, M. F. *Biomacromolecules* 2003, 4, 96. Recent investigations using cultured cells revealed PEMU properties important for cell biocompatibility. See Ito, Y.; Chen, G. P.; Imanishi, Y. *Bioconjugate Chemistry* 1998, 9, 277, Chluba, J.; Voegel, J. C.; Decher, G.; Erbacher, P.; Schaaf, P.; Ogier, J. *Biomacromolecules* 2001, 2, 800, Tryoen-Toth, P.; Vautier, D.; Haikel, Y.; Voegel, J. C.; Schaaf, P.; Chluba, J.; Ogier, J. *Journal of Biomedical Materials Research* 2002, 60, 657, Richert, L.; Lavalle, P.; Vautier, D.; Senger, B.; Stoltz, J. F.; Schaaf, P.; Voegel, J. C.; Picart, C. *Biomacromolecules* 2002, 3, 1170, Boura, C.; Menu, P.; Payan, E.; Picart, C.; Voegel, J. C.; Muller, S.; Stoltz, J. F. *Biomaterials* 2003, 24, 3521, Elbert, D. L.; Herbert, C. B.; Hubbell, J. A. *Langmuir* 1999, 15, 5355, and Serizawa, T.; Yamaguchi, M.; Akashi, M. *Biomacromolecules* 2002, 3, 724. These investigations have demonstrated that surfaces can be rendered cytophilic or cytophobic by embedding or attaching protein or peptides to the multilayer and by tuning the pH used for multilayer buildup. See Jessel, N.; Atalar, F.; Lavalle, P.; Mutterer, J.; Decher, G.; Schaaf, P.; Voegel, J. C.; Ogier, J. *Adv. Mater.* 2003, 15, 692 and Berg, M. C.; Yang, S. Y.; Hammond, P. T.; Rubner, M. F. *Langmuir* 2004, 20, 1362. Other modifications such as chemical cross-linking have improved the PEMU stability and cell adhesion. See Richert, L.; Boulmedais, F.; Lavalle, P.; Mutterer, J.; Ferreux, E.; Decher, G.; Schaaf, P.; Voegel, J.

C.; Picart, C. *Biomacromolecules* 2003. Certain surfaces such as polysaccharide films made by layer-by-layer buildup have been investigated for use as antimicrobial coatings and bioactive endovascular stent coatings. See Richert, L.; Lavalle, P.; Payan, E.; Shu, X. Z.; Prestwich, G. D.; Stoltz, J. F.; Schaaf, P.; Voegel, J. C.; Picart, C. *Langmuir* 2004, 20, 448 and Thierry, B.; Winnik, F. M.; Merhi, Y.; Silver, J.; Tabrizian, M. *Biomacromolecules* 2003, 4, 1564. In fact, polyelectrolyte complexes have a long history of use in preparing bioinert surfaces. See Tsuchida, E.; Abe, K. *Advances in Polymer Science* 1982, 45, 1, Philippe, B.; Dautzenberg, H.; Linow, K. J.; Kotz, J.; Dawydoff, W. *Progress in Polymer Science* 1989, 14, 91, and Petrak, K. *Journal of Bioactive and Compatible Polymers* 1993, 8, 178.

The surface properties of endovascular stents may play an important role in the process of restenosis. During restenosis, vascular smooth muscle cells migrate to cover implanted stents, often building layers of tissue that cause occlusion of the blood flow. See Indolfi, C.; Mongiardo, A.; Curcio, A.; Torella, D. *Trends in Cardiovascular Medicine* 2003, 13, 142. In evaluating biocompatibility, therefore, it is important to understand how smooth muscle cells interact with PEMU surfaces. Smooth muscle cells are capable of alternating between a 'contractile' phenotype, characterized by a non-motile cell type that possesses both a contractile smooth muscle cytoskeleton and a non muscle cytoskeleton for cell support, and a 'synthetic' phenotype that is motile and possesses a non-muscle cytoskeleton used for cell support and cell motility. See Worth, N. F.; Rolfe, B. E.; Song, J.; Campbell, G. R. *Cell Motility and the Cytoskeleton* 2001, 49, 130 and Halayko, A. J.; Solway, J. *Journal of Applied Physiology* 2001, 90, 358. The two cell phenotypes can be readily distinguished by the cell shape, stability of adhesion, and organization of the underlying cytoskeleton structures.

SUMMARY OF THE INVENTION

Among the aspects of this invention may be noted the provision of articles having thin films of polyelectrolyte complex thereon and methods for use of said articles. The thin films comprise interpenetrating networks of net positively charged compositions and net negatively charged compositions, the compositions comprising polyelectrolytes containing polymer repeat units having at least two fluorine atoms, polymer repeat units having zwitterions groups, or both. Said articles having thin films thereon are adapted to promote cell adhesion and growth, or to inhibit cell adhesion in living tissue or in marine environments.

Briefly, therefore, the invention is directed to an article adapted for use in combination with living tissue or in a marine environment, the article comprising: a substratum having a surface; and a polyelectrolyte film on the surface, the polyelectrolyte film comprising a network of a net positively charged composition and a net negatively charged composition, wherein the net positively charged composition comprises a net positively charged polyelectrolyte or the net negatively charged composition comprises a net negatively charged polyelectrolyte, and the net positively charged polyelectrolyte or the net negatively charged polyelectrolyte contain (i) a polymer repeat unit having at least two fluorine atoms, or (ii) a polymer repeat unit having a zwitterion group; wherein the substratum has a composition and shape adapting the article for use in combination with living tissue or in a marine environment.

The invention is further directed to an article adapted for use in combination with living tissue or organisms, the article comprising a polyelectrolyte film, the film comprising an interpenetrating network of a net positively charged polyelectrolyte and a net negatively charged polyelectrolyte, the film having first and second surface regions with a net positively charged or net negatively charged polyelectrolyte exposed at each of said first and second surface regions wherein (1) the net positively charged or negatively charged polyelectrolyte exposed in said first surface region contains a polymer repeat unit having at least two fluorine atoms and (2) the net positively charged or negatively charged polyelectrolyte exposed in said second surface region contains a polymer repeat unit having a zwitterion group.

The invention is yet further directed to a method for controlling the attachment and growth of cells on a surface of an article, the method comprising contacting the article with living tissue, living organisms, or with water in an aqueous system comprising living organisms wherein the article comprises a substratum having a surface and a film on the surface, the film comprising a network of a net positively charged composition and a net negatively charged composition, wherein the net positively charged composition comprises a net positively charged polyelectrolyte or the net negatively charged composition comprises a net negatively charged polyelectrolyte, and the net positively charged polyelectrolyte or the net negatively charged polyelectrolyte contain (i) a polymer repeat unit having at least two fluorine atoms, or (ii) a polymer repeat unit having a zwitterion group.

Other objects and aspects of the invention will be, in part, pointed out and, in part, apparent hereinafter.

BRIEF DESCRIPTION OF THE DRAWINGS

FIGS. 4A-4F are Axiocam phase images showing live A7r5 cells cultured on (A)(PFPVP/Nafion)$_2$, (B)(PDADMA/PSS)$_2$, (C)(PAH/PAA)$_2$, (D)(PFPVP/Nafion)$_2$PFPVP, (E)(PDADMA/PSS)$_2$PDADMA, and (F)(PAH/PAA)$_2$PAH according to the method of Example 6. Top panel are negatively charged surfaces (A-C). Bottom panel are positively charged surfaces (D-F). Hydrophobicity decreases from the left (A, D) panel to the right panel (C, F). Right bottom tags represent polymer on outermost surface (scale bar=20 µm).

Figure 7C:
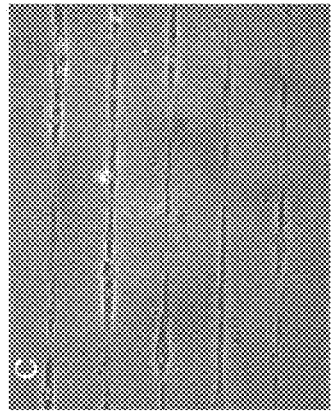
Figure 7B:
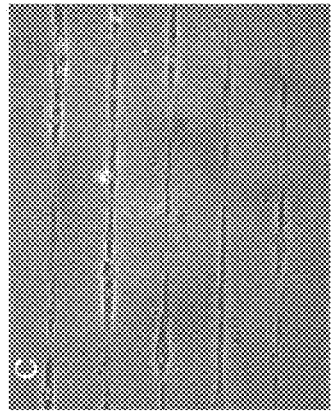
Figure 7A:
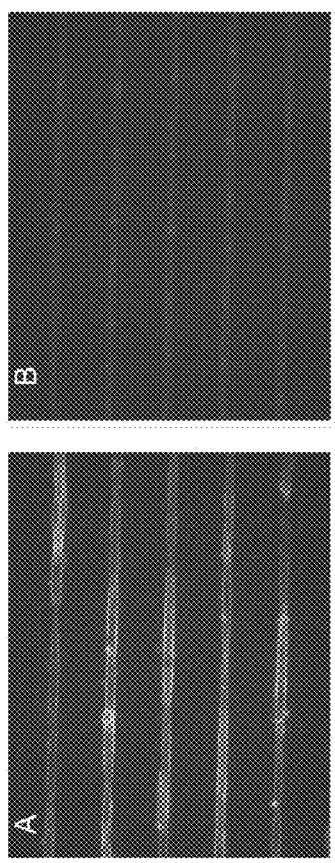

FIGS. 7A-7C are Axiocam phase images showing micropatterning of A7r5 cells grown on 20 μm wide ridges of Nafion® stamped on 80 μm wide troughs of 75:25 mol % PAA:PAEDAPS copolymer according to the method of Example 9.

(A) Fluorescently labeled phalloidin staining actin, (B) cell nuclei fluorescently labeled with DAPI, and (C) a phase image of the same micropatterned area (scale bar=80 μm).

Figure 8C:
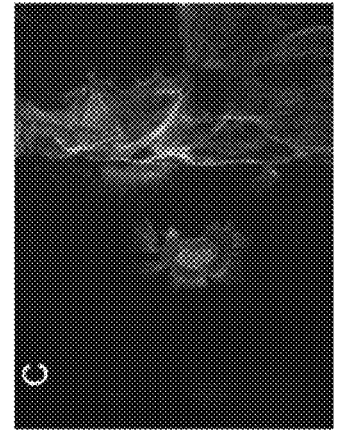
Figure 8B:
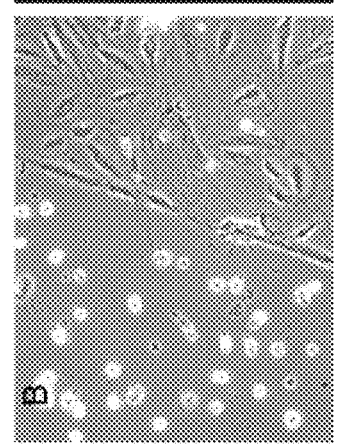
Figure 8A:
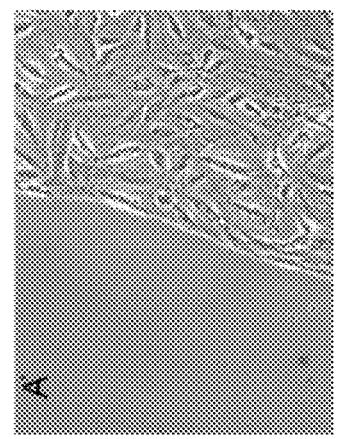

FIGS. 8A-8C are Axiocam phase images showing, according to the method of Example 10, (A) A7r5 cells growing on Nafion® (right) stamped onto PAA:PAEDAPS (75:25 mol %) copolymer (left) showing the interface where the cell adhesive (Nafion®) stamped surface meets the cell repulsive background surface (scale bar=20 μm), (B) A7r5 cells growing on Nafion® (right) stamped onto (PAH/PAA)$_2$PAH (left) (scale bar=20 μm), and (C) Fluorescently labeled phalloidin staining actin in A7r5 cells growing at the interface between the Nafion® stamp (right) and PAH background (left) (scale bar=10 μm).

FIGS. 9A-9E are Axiocam phase images showing unactivated human platelets adhering to polyelectrolyte coated cover slips: (A)(PAH/PAA)$_2$PAH, (B)(PFPVP/Nafion)$_2$, (C) (PAH/PAA)$_2$ (D) a 90:10 mol % copolymer mixture of PAA: AEDAPS, and (E) a 75:25 mol % copolymer mixture of PAA:AEDAPS according to the method of Example 11. Platelets are stained with Alexa 488 phalloidin. (bar=2.5 μm).

DETAILED DESCRIPTION OF THE PREFERRED EMBODIMENT(S)

The articles of the present invention are uniquely adapted for use in living tissue or aqueous systems comprising living organisms, said articles typically comprising a substratum and a polyelectrolyte film. The polyelectrolyte film comprises a network of a net positively charged composition and a net negatively charged composition. The net positively charged composition may be, for example, a net positively charged particle or polyelectrolyte and the net negatively charged composition may be, for example, a net positively charged particle or polyelectrolyte. In one preferred embodiment, the net positively charged composition comprises a net positively charged polyelectrolyte and the net negatively charged composition comprises a net negatively charged polyelectrolyte and the polyelectrolyte film is an interpenetrating network of the two polyelectrolytes. The composition of the polyelectrolyte may be varied to render the article suitable for enhancing the attachment and growth of cells in living tissue and aqueous systems, or conversely the composition of the polyelectrolyte may be varied to inhibit the attachment and growth of cells. Compositions of the present invention having surface regions comprising polyelectrolytes containing a polymer repeat unit having at least two fluorine atoms are uniquely suited to enhance cell attachment, growth, and even differentiation. Conversely, compositions having surface regions comprising polyelectrolytes containing a polymer repeat unit having a zwitterion group are suited to inhibit cell adhesion. The substratum has a composition and shape adapting the article for use in combination with living tissue or in a marine environment.

The articles comprising polyelectrolyte films disposed on a substrate or as free membranes which are designed to promote cell adhesion and growth may comprise net negatively charged fluorinated compositions, net positively charged fluorinated compositions, or both. Preferably, the polyelectrolyte film comprises both net positively and net negatively charged fluorinated compositions.

The net positively and net negatively charged fluorinated compositions for use in the polyelectrolyte films may comprise net positively and net negatively charged polyelectrolytes comprising fluorinated charged polymer repeat units (e.g., fluorinated and positively charged groups or fluorinated and negatively charged groups), fluorinated uncharged or neutral polymer repeat units, unfluorinated charged polymer repeat units (e.g., positively charged groups or negatively charged groups), or unfluorinated uncharged or neutral polymer repeat units (e.g., unfluorinated uncharged groups or unfluorinated zwitterion groups). The various types of repeat units are present in random, block, or graft co-polymers, or as homopolymers. Fluorinated polymer repeat units, either charged or uncharged, preferably comprise fluorine groups present as fluorinated conjugated groups, =CF—, fluorinated methylene groups, —CF$_2$—, or fluorinated methyl groups, —CF$_3$. These moieties may be present in fluorinated aliphatic groups, fluorinated olefinic groups, fluorinated aryl groups, or fluorinated heteroaryl groups. The fluorinated polymer repeat unit comprises at least 2 fluorine atoms. Typically, the fluorinated polymer repeat unit comprises between 2 and 21 fluorine atoms, more typically between 2 and 17 fluorine atoms, and even more typically between 2 and 13 fluorine atoms. Preferably, at least 5% of the polymer repeat units of the fluorinated polyelectrolyte comprise fluorinated groups. More preferably, at least 20% of the polymer repeat units comprise fluorinated groups.

The polyelectrolyte films comprising fluorinated repeat units of the present invention comprise at least two or more alternating layers, each layer characterized by a charge. For example, thin films can be built up by depositing a first layer having a net charge, then depositing a second layer having a net charge opposite that of the first layer. At least one of the layers comprises a net charged polyelectrolyte. For example, the thin film may comprise a blend of a net positively charged polyelectrolyte and a net negatively charged polyelectrolyte in an interpenetrating network. In another example, the net positively charged polyelectrolyte may comprise one net positively charged polyelectrolyte or a blend of two or more net positively charged polyelectrolytes, at least one positively charged polyelectrolyte containing fluorinated repeat units. Also, the net negatively charged polyelectrolyte may comprise one negatively charged polyelectrolyte or a blend of two or more net negatively charged polyelectrolytes, at least one negatively charged polyelectrolyte containing fluorinated repeat units. The thin films of the present invention may comprise a blend of two or more net positively charged and a blend of two or more net negatively charged polyelectrolytes. The blended polyelectrolytes preferably comprise at least one net positively charged polyelectrolyte which contains fluorinated repeat units, at least one net negatively charged polyelectrolyte which contains fluorinated repeat units, or both. Preferably, in such blends, at least 5% of the charged polyelectrolytes comprise fluorinated repeat units, and more preferably at least 20% of the polyelectrolytes in the blend comprise fluorinated repeat units.

In another embodiment, the polyelectrolyte film comprises net positively charged and net negatively charged compositions comprising a fluorinated particle having a charge. The polyelectrolyte film also comprises a fluorinated polyelectrolyte having an opposite charge of the fluorinated particle to form a composite of particles and polyelectrolyte. For example, particles may be formed of polytetrafluoroethylene (PTFE) or another polymer comprising polymer repeat units having at least two fluorine atoms. Preferably, the surface of the particles is constituted of polymers comprising polymer repeat units having at least two fluorine atoms, while the contents of the bulk of the particles are not narrowly critical. For example, the bulk of the particles may comprise fluorinated polymers, non-fluorinated polymers, or may even be hollow. Particles having an average particle size of less than about 100 nm tend to form stable colloids in water whereas particles having an average particle size of greater than about 100 nm tend to form unstable suspensions in water. These dispersions, whether colloidal or not, can be further stabilized by coating the particles with charged surfactants, thus imparting a net charge on the particles. The surfactants may be positively charged or negatively charged. Representative surfactants include alkyl sulfonates, alkyl sulfates such as sodium dodecyl sulfate, tetraalkylammonium such as alkyltrimethylammonium, or cetyl pyridinium. Particles constituted of polymers comprising polymer repeat units having at least two fluorine atoms at the surface and coated with a charged surfactant may be used as a charged layer in a thin film.

The articles comprising polyelectrolyte films disposed on a substrate or as free membranes which are designed to inhibit cell adhesion may comprise net negatively charged compositions comprising zwitterion groups, net positively charged compositions comprising zwitterion groups, or both. Preferably, the polyelectrolyte film comprises both net positively and net negatively charged zwitterionic compositions.

The net positively charged and net negatively charged compositions for use in polyelectrolyte films which inhibit cell adhesion may comprise net positively charged and net negatively charged polyelectrolytes comprising polymer repeat units having zwitterion groups, charged polymer repeat units, or neutral polymer repeat units. The various types of polymer repeat units are present in random, block, or graft co-polymers. Preferably, the polyelectrolytes comprise both zwitterion repeat units and charged repeat units. More preferably, the polyelectrolytes comprise zwitterion repeat units and carboxylic acid repeat units. In such co-polymers, the zwitterion repeat units constitute at least about 15 mole % of the co-polymer, preferably about 20 mole % to about 70 mole % of the co-polymer, more preferably between about 30 mole % to about 50 mole %.

The polyelectrolyte films comprising polymer repeat units having zwitterion groups comprise at least two or more alternating layers, each layer characterized by a charge. For example, thin films can be built up by depositing a first layer having a net charge, then depositing a second layer having a net charge opposite that of the first layer. At least one of the layers comprises a net charged polyelectrolyte. For example, the thin film may comprise a blend of a net positively charged polyelectrolyte and a net negatively charged polyelectrolyte in an interpenetrating network. In another example, the net positively charged polyelectrolyte may comprise one net positively charged polyelectrolyte or a blend of two or more net positively charged polyelectrolytes, at least one positively charged polyelectrolyte containing zwitterion repeat units. Also, the net negatively charged polyelectrolyte may comprise one negatively charged polyelectrolyte or a blend of two or more net negatively charged polyelectrolytes, at least one negatively charged polyelectrolyte containing zwitterion repeat units. The thin films may comprise a blend of two or more net positively charged and a blend of two or more net negatively charged polyelectrolytes. The blended polyelectrolytes preferably comprise at least one net positively charged polyelectrolyte which contains zwitterion repeat units, at least one net negatively charged polyelectrolyte which contains zwitterion repeat units, or both.

In another embodiment, the thin film comprises additional agents which further inhibit the adhesion of cells to the thin film comprising zwitterions repeat units. Such agents include paclitaxel and sirolimus. The articles adapted for use in combination with living tissue or organisms are characterized by a polyelectrolyte film having particular surface characteristics. In general, the article comprises a polyelectrolyte film comprising a network of a net positively charged composition and a net negatively charged composition. The net positively charged composition or the net negatively charged composition may comprise charged particles provided, however, the net negatively charged composition comprises a net negatively charged polyelectrolyte or the net positively charged composition comprises a net positively charged polyelectrolyte. In one preferred embodiment, the film is characterized by surface regions in which the net positively charged or net negatively charged polyelectrolyte exposed at the surface regions contains a polymer repeat unit having at least two fluorine atoms or a polymer repeat unit having a zwitterion group. It has been discovered that film modification such that the surface regions comprising the polymer repeat unit having at least two fluorine atoms or the polymer repeat unit having a zwitterion group is sufficient to control the attachment and growth of cells and that the characteristics of the bulk of the film are not narrowly critical to the film's cell attachment properties. The polyelectrolyte films may be present on substratum having a composition and shape adapting the article for use in combination with living tissue or in a marine environment, or the films may be present as free membranes. In one embodiment, the free membrane is a membrane having opposing sides, the first surface region being one of the opposing sides and the second surface region being the other opposing side. The net positively charged or negatively charged polyelectrolyte exposed in said first surface region contains a polymer repeat unit having at least two fluorine atoms and the net positively charged or negatively charged polyelectrolyte exposed in said second surface region contains a polymer repeat unit having a zwitterion group. In another embodiment, the free membrane or film on a substratum is characterized by a first surface region and a second surface region have substantially planar exposed surfaces wherein the first and second surface regions are substantially contiguous so as to define a pattern of regions having water contact angles that differ by at least 30 degrees.

Cytophilicity is a term used to describe whether a cell shows an affinity for a surface, said affinity demonstrated by the adhesion of the cell to the surface and, at the extreme of affinity, by the spreading and differentiation of a cell into its biologically functional form. The creation of surfaces having a range of cytophilicity, an object of this invention, is accomplished using thin films of polyelectrolyte complex. Cytophilic surfaces are preferably prepared from polyelectrolyte complex comprising fluorinated polyelectrolytes. Cytophobic, or cell-repelling, surfaces are preferably prepared from polyelectrolyte complex comprising zwitterionic and charged repeat units.

It is known by those skilled in the art that cell adhesion and growth on a particular surface, including those surfaces comprising polymers, cannot be predicted a priori. For example, "So far, no general principles that would allow prediction of the extent of attachment, spreading or growth of cultured cells on polymer surfaces have been identified" from W. M. Saltzman in "Principles of Tissue Engineering," 2nd Ed., Eds. R. P. Lanza, R. Langer, J. Vacanti, Academic Press, San Diego, 2000. On the other hand, rough guidelines apply. For example, cell adhesion appears to be maximized on surfaces with intermediate wettability (See Y. Tamada & Y. Ikada, J.

*Biomed. Mater. Res.* 28, 783 (1994)). Fluorinated surfaces fall into the highly hydrophobic category, and thus the utility of fluorinated polyelectrolytes for cell adhesion and growth is unexpected. For example, Hyde et al. (*J. Indust. Microbiol. Biotech.* 19, 142 (1997)) describe the effectiveness of fluorinated polymers at diminishing biofilm adherence to steel, polypropylene, and glass. The utility of fluorinated polyelectrolytes, which are distinctly non-biological materials, in promoting adhesion and growth of cells was unexpected. In particular, it could be reasoned that the positive polyelectrolyte might mimic the behavior of positive surfactant-type molecules by disrupting the cell membrane and compromising cell integrity. However, no evidence for dead cells on the perfluorinated surfaces could be found. Without being held to a particular theory, it is possible that cells respond as they do to the hydrophobic nature of the perfluorinated surface, while the "fluorophobic" qualities of the cell membranes prevent them from mixing with the multilayer components. Indeed, phase separations of perfluorinated hydrocarbons from other (nonfluorinated) hydrophobic molecules are common.

Preferred embodiments of this invention aid in precise control of interfacial solid/solution properties. Thus, in one preferred embodiment of this invention, a polyelectrolyte complex comprising at least one positive and at least one negative polyelectrolyte, wherein at least one of the polyelectrolytes is fluorinated, forms a film on the surface of and in contact with a substrate. Preferably, the last-added, or "top" layer of said complex comprises fluorinated polyelectrolyte. Biological cells adhere, and grow on, said polyelectrolyte complex. Preferably, the fluid contacting said polyelectrolyte complex also contains essential nutrients, buffer ions, and other chemical and biochemical species known by those skilled in the art to promote the attachment, spreading, differentiation, and proliferation of said cells. Examples of growth media are provided below.

Preferred cells for growth on the polyelectrolyte complex comprising fluorinated polyelectrolyte include smooth muscle cells, neuronal (nerve) cells, epithelial cells, and stem cells.

Preferred substrates on which the polyelectrolyte complex thin films of this invention are deposited include stents, catheters, vascular grafts and prostheses, ocular prostheses such as contact lenses and intraocular implants, artificial valves for in vivo use, and other articles implanted either short-term or long-term in vivo, such as artificial organs, dental implants, metal implants into bone, and metal objects adapted for use in aqueous systems containing living organisms.

A further preferred substrate on which the polyelectrolyte complex thin films of this invention are deposited is a corneal implant. Preferred materials for said implant are hydroxyethylmethacrylate and copolymers thereof.

Further preferred substrates are cell and tissue culturing substrates, such as Petri dishes, roller bottles, microcarriers, porous structural supports for three dimensional cell growth, and similar cell and tissue growth templates.

A. Polyelectrolytes for Multilayer Films

The oppositely charged polymers (i.e., polyelectrolytes) used to form the films are water and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative, and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly(diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive and negative repeat units distributed throughout the polymer in a random, alternating, or block sequence. These polyelectrolytes are termed "amphiphilic" polyelectrolytes. For example, a polyelectrolyte molecule may comprise 100 randomly distributed styrene sulfonate repeat units (negative) and 100 diallyldimethylammonium chloride repeat units (positive), said molecule having a net charge of zero.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic. An example of a zwitterionic repeat unit is 3-[2-(acrylamido)-ethyldimethyl ammonio]propane sulfonate, AEDAPS. Zwitterion groups are present on polyelectrolytes as blocks or randomly dispersed throughout the polymer chain. Preferably, polyelectrolytes comprise at least about 15 mole % zwitterions repeat units, preferably between about 20 mole % and about 70 mole % zwitterion units, and more preferably said polyelectrolytes comprise between about 30 mole % and about 50 mole % zwitterion units. Preferred compositions of polyelectrolytes comprising zwitterionic repeat units also comprise between about 10% and about 90% non-zwitterionic charged repeat units.

The charges on a polyelectrolyte may be derived directly from the monomer units or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($—SO_3^-$), such as poly(styrenesulfonic acid) (PSS), poly(2- acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof; and polycarboxylates such as poly(acrylic acid) (PAA) and poly(methacrylic acid).

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; and protonated polyamines such as poly(allylaminehydrochloride) (PAH) and polyethyleneimine (PEI).

Some synthetic polyelectrolytes used in accordance with the present invention generally become charged at certain pH values. For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivatives thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte of a polyelectrolyte at the surface of, or within, a polyelectrolyte multilayer.

The state of ionization, or average charge per repeat unit, for polyelectrolytes bearing pH-sensitive groups depends on the pH of the solution. It is understood that the term "pH-sensitive," as applied to a functional group, refers to a functional group that exhibits differing degrees of ionization over the working pH range of the experiment, while "pH-insensitive" refers to functional groups that maintain the same charge (either positive or negative) over the working pH range of the experiment. For example, a polyelectrolyte molecule comprising 100 pH-insensitive positively charged units, such as diallyldimethylammonium, DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte typically comprises about 0.01% to about 40% by weight of a polyelectrolyte solution, and preferably about 0.1% to about 10% by weight.

The polyelectrolytes of the present invention comprise polymer chain backbone units and pendant groups from the polymer chain backbone units. Polymer chain backbone units for use in the thin films of the present invention are preferably polyolefin groups (e.g., vinyl or allyl groups). Other polymer chain backbones units which may be applicable include polyamines, polyamides, polyethers, polyesters, polyimides, polysulfones, polyaryls, polyphenols, polyaramides, and copolymers thereof.

Many polyelectrolytes, such as PDADMA and PEI, exhibit some degree of branching. Branching may occur at random or at regular locations along the backbone of the polymer. For example, for the polymer repeat unit PDADMA, branching may occur due to the presence of two allyl groups on the quaternary nitrogen. For PEI, branching may occur at secondary nitrogen groups along the polymer backbone. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention.

Many of the foregoing polyelectrolytes have a very low toxicity. In fact, poly(diallyldimethylammonium chloride), poly(2-acrylamido-2-methyl-1-propane sulfonic acid), and their copolymers are used in the personal care industry, e.g., in shampoos. Also, because the polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNOVP) is considered to be hydrophilic, whereas polyvinyl pyridine alkylated with an octyl group (PNOVP) is considered to be hydrophobic. Thus, water is preferably used as the solvent for hydrophilic polyelectrolytes, and organic solvents such as ethanol, methanol, dimethylformamide, acetonitrile, carbon tetrachloride, and methylene chloride are preferably used for hydrophobic polyelectrolytes. Preferred solvents for fluorinated polymers are themselves fluorinated. Another preferred solvent for fluorinated polymers is supercritical carbon dioxide. Since some solvents are known to be incompatible with some plastic materials, preferred solvents for depositing polyelectrolyte complex thin films on plastics are water and alcohols.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group, such as, poly(N-methylvinylpyridium); and protonated polyamines, such as, poly(allylamine hydrochloride) and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonic acid), poly(diallyldimethylammonium chloride), poly(N-methylvinylpyridinium), and poly(ethyleneimine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate. Preferred counterions that assist the solubility of polyelectrolytes in organic solvents of low dielectric constant, and in supercritical $CO_2$, include perfluorinated alkane sulfonates, preferably of length from 3 to 10 carbons, and perfluoroalkane carboxylic acids, preferably of length from 3 to 18 carbons.

In some applications, the PEMU preferably inhibits cell adhesion and growth. Substrates for which it is advantageous to inhibit cell adhesion and growth include ocular prostheses such as contact lenses and intraocular lenses, vascular grafts and prostheses, artificial organs, and stents. In order to minimize adhesion of cells on articles implanted in vivo, preferred polyelectrolyte complex coatings for inhibiting cell adhesions on articles comprise polyelectrolyte molecules comprising zwitterion repeat units and net charged repeat units.

Preferred net charged repeat units include sulfonates, styrenesulfonates, 2-acrylamido-2-methyl-1-propane sulfonic acid, ethylenesulfonic acid, methacryloxyethylsulfonic acid, sulfonated ether ether ketone, diallyldialkylammonium, vinylbenzyltrimethylammonium, ionenes, acryloxyethyltrimethyl ammonium chloride, methacryloxy(2-hydroxy)propyltrimethyl ammonium, N-methylvinylpyridinium, other N-alkylvinyl pyridiniums, N-aryl vinyl pyridiniums, alkyl- or aryl imidazolium, carboxylates such as acrylic acid and methacrylic acid, phosphates, protonated pyridines, protonated imidazoles, and protonated primary, secondary, or tertiary amines. Table I below depicts the names and structures of net charged repeat units which may be incorporated into copolymers also comprising zwitterionic repeat units.

TABLE I

Net Charged Repeat Units for use in Polyelectrolytes

| Name | Structure |
| --- | --- |
| Diallyldimethylammonium (PDADMA) | 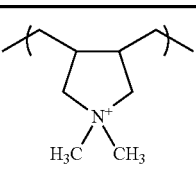 |
| Styrenesulfonic acid (PSS) | 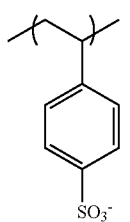 |

TABLE I-continued

Net Charged Repeat Units for use in Polyelectrolytes

| Name | Structure |
| --- | --- |
| Acrylic acid (PAA) | 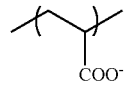 |
| Allylamine (PAH) | 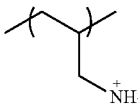 |
| N-methyl-2-vinyl pyridinium (PM2VP) | 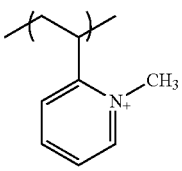 |
| Methacrylic acid (PMA) | 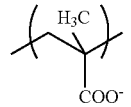 |

Examples of zwitterionic repeat units include N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl) carboxymethyl methylsulfonium chloride, 1-(3-sulfopropyl)-2-vinylpyridinium betaine, N-(4-sulfobutyl)-N-methyl-N,N-diallylamine ammonium betaine (MDABS), N,N-diallyl-N-methyl-N-(2-sulfoethyl) ammonium betaine, N,N-dimethyl-N-(3-methacrylamidopropyl)-N-(3-sulfopropyl) ammonium betaine, N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-methacryloyloxyethyl-N-(3-sulfopropyl)-ammonium betaine, and N,N-dimethyl-N-(3-methacrylamidopropyl)-N-(3-sulfopropyl) ammonium betaine.

More preferably, said polyelectrolyte complexes comprise both carboxylic acid and zwitterionic repeat units. Preferably, the zwitterionic and carboxylic acid groups are on the same polyelectrolyte molecule, or copolyelectrolyte. The preferred zwitterion content on said copolyelectrolytes is at least about 15 mole percent, preferably between about 20 mole percent and about 70 mole percent, more preferably between about 30 mole percent and about 50 mole percent, with carboxylic acid units preferably comprising the balance of the copolyelectrolyte.

Preferred zwitterionic repeat units include 3-[2-(acrylamido)-ethyldimethyl ammonio]propane sulfonates (AEDAPS). Preferred copolymers comprising a net charged repeat units and zwitterionic repeat units include poly(acrylic acid)-co-poly(3-[2-(acrylamido)-ethyldimethyl ammonio] propane sulfonate), PAA-co-PAEDAPS. Since zwitterion groups are net charge neutral, they interact only weakly with charged groups. Thus, the preferred amount of zwitterion repeat unit should be not so high that the copolymer does not form complexes with oppositely-charged polyelectrolyte. The maximum percentage of zwitterion unit that can be tolerated depends on the chemical identity of the net charged unit that is holding the polyelectrolyte complex together. Preferred mole percentages of zwitterion do not exceed about 80 mole %, unless provision for chemical crosslinking is made during or after multilayer formation. The polymer repeat unit having a zwitterion group is preferably located on a polyelectrolyte molecule that also comprises a net charged repeat unit, preferably a carboxylic acid, preferably acrylic acid. Table II shows the structures of preferred zwitterionic repeat units for use in membranes for inhibiting cell adhesion.

TABLE II

Zwitterion Repeat Units for use in Polyelectrolytes

| Name | Structure |
|---|---|
| 3-[2-(acrylamido)-ethyldimethyl ammonio] propane sulfonate (AEDAPS) | (structure) |
| N-propane sulfonate-2-vinyl-pyridine (P2PSVP) | (structure) |

Optionally, the polyelectrolytes comprise an uncharged repeat unit that is preferably hydrophilic. Preferred uncharged hydrophilic repeat units are acrylamide, vinyl pyrrolidone, ethylene oxide, and vinyl caprolactam. The structures of exemplary uncharged repeat units are shown in Table III.

TABLE III

Uncharged Repeat Units for use in Polyelectrolytes

| Name | Structure |
|---|---|
| Acrylamide | (structure) |
| Vinylpyrrolidone | (structure) |
| Ethylene Oxide | (structure) |
| Vinylcaprolactam | (structure) |

In order to further inhibit growth of cells that may have attached to articles coated with films of polyelectrolyte complexes comprising copolyelectrolytes of zwitterionic and carboxylic acid repeat units, said films preferably further comprise paclitaxel or sirolimus or other agents known to those skilled in the art to inhibit cell growth and proliferation. Substrates for which it is advantageous to include agents known to inhibit cell growth and proliferation include stents, catheters, vascular grafts, vascular prostheses, contact lenses, intraocular implants, artificial valves for in vivo use, and artificial organs. Preferably, the film of polyelectrolyte complex comprising zwitterionic repeat units (hydrophilic) is deposited on a hydrophobic stratum, said hydrophobic stratum enhancing the adhesion of the hydrophilic stratum to the substrate and also enhancing the uptake of agents such as paclitaxel and sirolimus. Since these agents are relatively hydrophobic, they will partition more strongly into hydrophobic strata.

In another preferred embodiment of this invention, the surface of a substrate is coated with a thin film of polyelectrolyte complex comprising a zwitterionic repeat unit, and the coating is used to prevent or reduce the adsorption of platelets, bacteria, and marine microorganisms. Films which reduce the adsorption of platelets are advantageous for coating stents. Antimicrobial films are advantageous for coating contact lenses, intraocular lenses, vascular grafts, catheters, artificial organs, and stents.

Films for which it is advantageous to reduce the adsorption of marine organisms are useful for coating metal surfaces adapted for use in aqueous systems having living organisms. Such substrates that are routinely exposed to water include, for example, the hull of a ship. In these applications, the highly hydrophilic polyelectrolytes having polymer repeat units having zwitterion groups may enhance corrosion of the metal substrate. Therefore, it is preferred to deposit a first stratum of polyelectrolyte complex comprising polymers having fluorinated repeat units onto the surface of the metal substrate to control and thereby enhance the hydrophobicity of the metal substrate, which additionally imparts corrosion resistance. After the first stratum of polyelectrolyte complex comprising fluorinated repeat units is deposited, a second stratum of polyelectrolyte complex comprising polymers having zwitterion groups may be deposited to inhibit the adsorption of marine organisms.

In some applications, the polyelectrolyte film preferably enhances cell adhesion, growth, and in some embodiments differentiation. Substrates for which it is advantageous to enhance cell adhesion, growth, and differentiation include vascular grafts and catheters where the growth of endothelial cells on the surface of the graft or catheter renders the graft or catheter biocompatible, dental implants, cell and tissue culturing substrates, and metal implants into bone. Preferred polyelectrolyte film coatings for inducing cell adhesion and growth on complex objects comprise fluorinated polymers.

The fluorinated polyelectrolytes comprising the polyelectrolyte thin films of this invention are preferably copolymers, or copolyelectrolytes, comprising fluorinated and non-fluorinated repeat units. Said repeat units may be disposed in a random or block fashion on the backbone of said copolyelectrolytes. Preferred fluorinated copolyelectrolytes comprise charged non-fluorinated with noncharged fluorinated repeat units, or charged fluorinated with noncharged nonfluorinated repeat units. Other preferred fluorinated polyelectrolytes comprise charged fluorinated repeat units with charged non-fluorinated repeat units. Fluorinated copolyelectrolytes are preferably made by post-polymerization reactions on polymers, such as alkylation, or by polymerization of fluorinated monomers or mixtures of fluorinated monomers. Mole percentages of fluorinated repeat units on fluorinated copolyelectrolytes are preferably from 10% to 95%, and more preferably from 20% to 95%.

The fluorinated polyelectrolytes of the present invention are hydrophobic, preferably having water/air/surface interfacial contact angles greater than about 70 degrees, more preferably greater than about 80 degrees, and even more preferably greater than about 90 degrees. Measurement of the interfacial contact angle between a water surface and a coated surface is a well known method of assessing the wetting properties of water on a material (see R. J. Good, *J. Adhesion Sci. Technol.*, 12, 1269, (1992)). If the contact angle of water on a coating is low, the surface is said to be hydrophilic. If the contact angle is high, the surface is said to be hydrophobic. Surfaces with contact angles of greater than 90 degrees are particularly effective for antiwetting applications. The contact angle of water on polyelectrolyte multilayers depends on the combination of polyelectrolytes and also on which polyelectrolyte is used for the "top" layer (see for example Chen and McCarthy, *Macromolecules*, 30, 78 1997; and Yoo et al. *Macromolecules*, 31, 4309 (1998)).

Preferred fluorinated polyelectrolytes are either positive or negative. A range of repeat units may be included in the predominantly positively charged polymer, the predominantly negatively charged polymer, or both. In one embodiment, the repeat unit is a positively charged repeat unit comprising groups selected from the group consisting of a quaternary nitrogen atom ($N^+$), a sulfonium ($S^+$) atom, or a phosphonium atom ($P^+$). Thus, for example, the quaternary nitrogen may be part of a quaternary ammonium moiety (—$N^+R_aR_bR_c$ wherein $R_a$, $R_b$, and $R_c$ are independently alkyl, aryl, or mixed alkyl and aryl), a pyridinium moiety, a bipyridinium moiety, or an imidazolium moiety, the sulfonium atom may be part of a sulfonium moiety (—$S^+R_dR_e$ wherein $R_d$ and $R_e$ are independently alkyl, aryl, or mixed alkyl and aryl) and the phosphonium atom may be part of a phosphonium moiety (—$P^+R_fR_gR_h$ wherein $R_f$, $R_g$, and $R_h$ are independently alkyl, aryl, or mixed alkyl and aryl). In another embodiment, the repeat unit is a negatively charged repeat unit comprising groups selected from the group consisting of sulfonates (—$SO_3^-$, phosphates (—$OPO_3^-$, or sulfates (—$SO_4^-$). For illustrative purposes, certain of these moieties are shown as vinyl repeat units:

Vinyl Polymer Repeat Unit

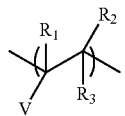

wherein $R_1$, $R_2$, and $R_3$ are each independently: —$(CH_2)_m$H or —$(CH_xF_{2-x})_nF$ and m and n are independently 0 to 12, x is 0, 1, or 2 and V is a group selected from among the following:

fluorinated hydrocarbons having the structure: —$(CH_2)_p(CF_2)_qF$, —$(CH_2)_p(CF_2)_qCOOH$, —$(CH_2)_p(CF_2)_qOPO_3^-$, —$(CH_2)_p(CF_2)_qSO_3^-$, —$(CH_2)_p(CF_2)_qOSO_3^-$, —$O(CH_2)_p(CF_2)_qF$, —$O(CH_2)_p(CF_2)_qSO_3^-$ and wherein p is 0 to 6 and q is 1 to 21;

fluorinated amides having the structure:

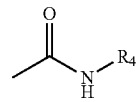

wherein $R_4$ is —$(CH_2)_p(CF_2)_qF$, —$(CH_2)_p(CF_2)_qCOOH$, —$(CH_2)_p(CF_2)_qOPO_3^-$—$(CH_2)_p(CF_2)_qSO_3^-$, —$(CH_2)_p(CF_2)_qOSO_3^-$ and wherein p is 0 to 6 and q is 1 to 21;

fluorinated esters having the structure:

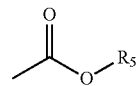

wherein $R_5$ is —$(CH_2)_p(CF_2)_qF$, —$(CH_2)_p(CF_2)_qCOOH$, —$(CH_2)_p(CF_2)_qOPO_3^-$—$(CH_2)_p(CF_2)_qSO_3^-$, —$(CH_2)_p(CF_2)_qOSO_3^-$ and wherein p is 0 to 6 and q is 1 to 21;

fluorinated phenyl groups having the structure:

wherein n is 2 to 5; or

wherein $R_6$ is—$(CH_2)_p(CF_2)_qF$ or —$O(CH_2)_p(CF_2)_qF$ and wherein p is 0 to 6 and q is 1 to 21;

fluorinated pyridiniums having the structure:

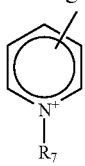

wherein $R_7$ is $-(CH_2)_p(CF_2)_qF$ and wherein p is 0 to 6 and q is 1 to 21;

fluorinated imidazoliums having the structure:

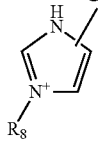

wherein $R_8$ is $-(CH_2)_p(CF_2)_qF$ and wherein p is 0 to 6 and q is 1 to 21;

fluorinated quaternary nitrogens having the structure:

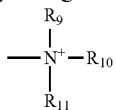

wherein $R_9$, $R_{10}$, and $R_{11}$ are each independently $-(CH_2)_p(CF_2)_qF$ wherein p is 0 to 6 and q is 1 to 21 or -arylF$_z$ wherein z is 2 to 8;

fluorinated sulfoniums having the structure:

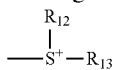

wherein $R_{12}$ and $R_{13}$ are each independently $-(CH_2)_p(CF_2)_qF$ wherein p is 0 to 6 and q is 1 to 21 or -arylF$_z$ wherein z is 2 to 8; and fluorinated phosphoniums having the structure:

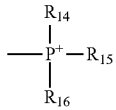

wherein $R_{14}$, $R_{15}$, and $R_{16}$ are each independently $-(CH_2)_p(CF_2)_qF$ wherein p is 0 to 6 and q is 1 to 21 or arylF$_z$ where z=2 to 8.

For illustrative purposes, certain of these moieties are shown as allyl repeat units (e.g., PDADMA):

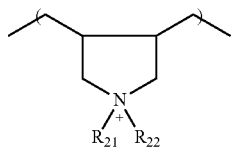

wherein $R_{21}$ and $R_{22}$ are $-(CH_2)_p(CF_2)_qF$, wherein p and q are independently selected for $R_{21}$ and $R_{22}$, and p is 0 to 6 and q is 1 to 21.

The positive fluorinated polyelectrolytes of this invention are preferably prepared by the alkylation of a nitrogen group, a sulfur group, or a phosphorus group by an alkylating molecule comprising two or more fluorine atoms. Said alkylating molecule also comprises a group that may be displaced on reaction (a "leaving group") that is well known to those skilled in the art. Examples of preferred leaving groups are chloride, bromide, iodide, and toluene sulfonate. Preferred nitrogen-containing groups on polymers to be alkylated are the pyridine group, imidazoles, and primary, secondary, or tertiary amines. Advantageously, alkylation often proceeds with the simultaneous creation of a positive charge. For efficiency of alkylation, preferred fluorinated hydrocarbons have one or two carbons that do not bear fluorines next to the leaving group.

Preferably, fluorinated copolyelectrolytes comprising charged fluorinated groups and charged unfluorinated groups are formed by the alkylation of residual nitrogen groups, sulfur groups, or phosphorus groups that were not fluorinated by the fluorinated alkylating agent. Alkylation reactions with fluorinated molecules are incomplete, typically reaching yields of less than 100%, typically about 50%. As a result, a fraction of the nitrogen, sulfur, or phosphorous groups are positively charged and comprise fluorinated hydrocarbons, while the remaining fraction is uncharged. Advantageously, the degree of charge can be controlled and increased by further alkylating the residual nitrogen groups, preferably with saturated non-fluorinated hydrocarbons comprising a leaving group as is known to those skilled in the art. Preferably, alkylation with the fluorinated molecules occurs before alkylation with the saturated hydrocarbons.

Preferred uncharged fluorinated monomers include fluorovinyl ethers, such as $CF_2=CF(OC_2F_4)_n-R$ where n is from 1 to 12 and R is a hydroxyl; alkoxy; aryl; or alkyl group, fluorinated styrenes, fluorinated olefins, vinylperfluoroesters, and vinylperfluoracrylates.

Preferred anionic fluorinated polyelectrolytes comprise the sulfonate group. Preferred anionic fluorinated polyelectrolytes comprising the sulfonate group are poly perfluorinated sulfonated ionomers including a polymer marketed under the trade name Nafion™ and sulfonated perfluorinated alkylvinyl vinyl ethers. Other preferred anionic polyelectrolytes comprise perfluorinated vinyl carboxylic acids. Table IV shows the structures of fluorinated polyelectrolytes for using in building PEMUs of the present invention.

TABLE IV

Fluorinated Polyelectrolyte Repeat Units for use in Fluorinated Polyelectrolytes

| Name | Structure |
|---|---|
| 4-vinyl-trideca-fluoro-octyl pyridinium iodide-co-4-vinyl pyridine (PFPVP) | 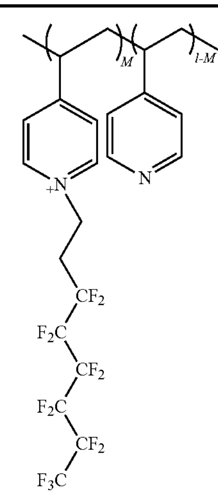 |

M is a mole fraction typically from about 0.1 to about 1.0, preferably from about 0.3 to about 0.8

TABLE IV-continued

Fluorinated Polyelectrolyte Repeat Units for use in Fluorinated Polyelectrolytes

| Name | Structure |
|------|-----------|
| NAFION | 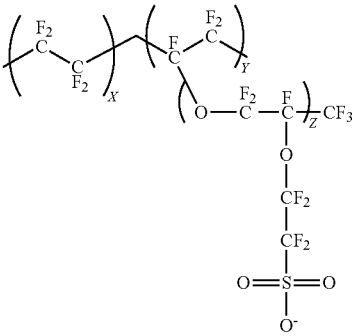 Where X, Y, and X denote molar proportions; X may be from about 6 to about 10 parts, Y may be about 1 part and Z may be from about 1 to about 3 parts |

Preferred charged nonfluorinated polyelectrolyte repeat units include sulfonates, styrenesulfonates, 2-acrylamido-2-methyl-1-propane sulfonic acid, ethylenesulfonic acid, methacryloxyethylsulfonic acid, sulfonated ether ether ketone, diallyldialkylammonium, vinylbenzyltrimethylammonium, ionenes, acryloxyethyltrimethyl ammonium chloride, methacryloxy(2-hydroxy)propyltrimethyl ammonium, N-methylvinylpyridinium, other N-alkylvinyl pyridiniums, N-aryl vinyl pyridiniums, alkyl- or aryl imidazolium, protonated pyridines, protonated imidazoles, and protonated primary, secondary, or tertiary amines. More preferred nonfluorinated charged repeat units include carboxylates such as acrylic acid and methacrylic acid, vinyl phosphates, and vinylphospholipids.

Table V below depicts the names and structures of repeat units which may be incorporated as uncharged or charged, fluorinated or unfluorinated repeat units in the polyelectrolytes for use in building the thin films of the present invention.

TABLE V

Repeat Units for use in Fluorinated Polyelectrolytes

| Name of Base Structure | Unalkylated Repeat Unit | Fluorinated Alkylated Repeat Unit | Unfluorinated Alkylated Repeat Unit |
|---|---|---|---|
| Diallyl ammonium (PDADMA) | 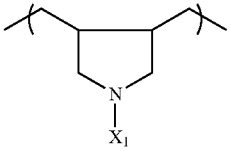 $X_1 = —(CH_2)_nCH_3$ <br> n = 0 to 18 | 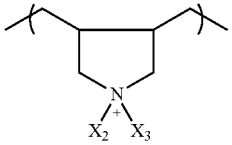 $X_2,X_3 = —(CH_2)_p(CF_2)_qF$ <br> p = 0 to 6 <br> q = 1-21 | 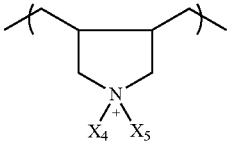 $X_4,X_5 = —(CH_2)_nCH_3$ <br> n = 0 to 18 |
| Styrene sulfonic acid (PSS) | 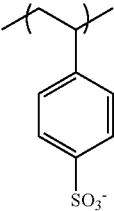 | | |
| Allyl amine (PAH) | 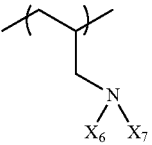 $X_6,X_7 = $ H or $—(CH_2)_nCH_3$ <br> n = 0 to 18 | 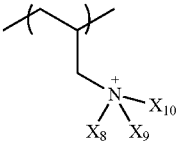 $X_8,X_9,X_{10} = $ <br> $—(CH_2)_p(CF_2)_qF$ <br> p = 0 to 6 <br> q = 1-21 | 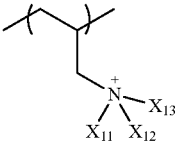 $X_{11},X_{12},X_{13} = $ H <br> or $—(CH_2)_nCH_3$ <br> n = 0 to 18 |

TABLE V-continued

Repeat Units for use in Fluorinated Polyelectrolytes

| Name of Base Structure | Unalkylated Repeat Unit | Fluorinated Alkylated Repeat Unit | Unfluorinated Alkylated Repeat Unit |
|---|---|---|---|
| Vinyl pyridine (PVP) | | $X_{14} =$ —$(CH_2)_p(CF_2)_qF$ $p = 0$ to $6$ $q = 1\text{-}21$ | $X_{15} =$ —$(CH_2)_nCH_3$ $n = 0$ to $18$ |
| Dialkyl amino Ethyl acrylamido | $X_{16}, X_{17} =$ H or —$(CH_2)_nCH_3$ $n = 0$ to $18$ | $X_{18}, X_{19}, X_{20} =$ —$(CH_2)_p(CF_2)_qF$ $p = 0$ to $6$ $q = 1\text{-}21$ | $X_{21}, X_{22}, X_{23} =$ H or —$(CH_2)_nCH_3$ $n = 0$ to $18$ |

In order to enhance the adhesion of polyelectrolyte complex thin films comprising fluorinated polyelectrolyte to a substrate, an intermediate nonfluorinated polyelectrolyte layer, or a stratum of nonfluorinated polyelectrolyte complex, is placed between said thin film and the substrate. Preferred polyelectrolytes for this intermediate stratum or layer include polyethyleneimine and poly(N-alkylvinylpyridiniums), where the N-alkyl group comprises 4 to 18 carbons. Said poly(N-alkylvinylpyridiniums) are organic-soluble and, having a hydrophobic character intermediate between a water-soluble polyelectrolyte and a fluorinated polyelectrolyte, enhance the adhesion of the fluorinated polyelectrolyte to a substrate.

It is known by those skilled in the art that the top, or outer, layer of a polyelectrolyte layer has the most effect on surface hydrophobicity. Accordingly, in one embodiment of this invention, the initial layers 0 through n of a multilayer are prepared from nonfluorinated polyelectrolytes, preferably those listed above, and the n+1 and n+2 layers comprise fluorinated positive polyelectrolyte and fluorinated negative polyelectrolyte. The use of fluorinated polyelectrolytes in only the top layers conserves potentially costly materials.

In another embodiment of this invention, the initial layers 0 through n of a multilayer are prepared from nonfluorinated polyelectrolytes, preferably those listed above, and the n+1 layer comprises fluorinated positive polyelectrolyte, preferably PFPVP. The contact angle of water on a PFPVP surface is higher than the contact angle on a Nafion surface. Therefore, a single layer of PFPVP is advantageously more hydrophobic than a single layer of Nafion.

In one embodiment of this invention, an article to be implanted in vivo is first coated with a film of polyelectrolyte complex comprising fluorinated polyelectrolyte, the outer layer of said film preferably comprising fluorinated polyelectrolyte, and then the article is coated with a layer of protein found in the animal into which the article is to be implanted. Preferably, said protein is serum albumin. A coating of serum albumin will render the article more biocompatible.

In yet another preferred embodiment of this invention, a thin film of polyelectrolyte complex comprising fluorinated repeat units also comprises polynucleic acids, such as DNA and RNA. Cells are then cultured onto this surface and the nucleic acid material preferably transfects into the cell, modifying the genetic material of said cell. The genes corresponding to the polynucleic acid are preferably expressed by the cell, leading to the production of select proteins. Preferably, the polynucleic acid is adsorbed to the surface of the polyelectrolyte complex film comprising fluorinated polyelectrolyte. More preferably, a complex of the polynucleic acid and a positively charged fluorinated polyelectrolyte are formed on the surface of a stamp and said complex is transferred directly to a surface by stamping. A positive fluorinated polyelectrolyte is preferred over a negative fluorinated polyelectrolyte because genetic material (i.e., DNA and RNA) is negatively charged and will therefore complex with positively charged polyelectrolyte. Optionally, the fluorinated polyelectrolyte complex film comprising polynucleic acid is coated on the surface of a scaffold, preferably comprising one of the biodegradable polymers listed below. Said coated scaffold encourages simultaneously the growth of cells and the transfection of genetic material from the scaffold to the growing cells.

To assist in maintaining the physical integrity of the polyelectrolyte thin film, in one preferred embodiment a small amount of chemical crosslinking is introduced into the film. Crosslinking is preferably accomplished by including difunctional monomers in the polyelectrolytes comprising the thin film. For example, a divinyl repeat unit added to the polymerization reaction will be incorporated into two polyelectrolyte chains, giving a crosslink at the connection point. Alternatively, a polyelectrolyte film may be treated with a difunctional crosslinking agent. A preferred crosslinking agent is a dihalogenated compound, such as an aromatic or aliphatic dibromide, which is able to alkylate residual unalkylated units on two adjoining polyelectrolyte chains. Another preferred method of crosslinking a formed polyelectrolyte thin film is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (*Macromolecules*, 36, 8590 (2003)) is by the addition of a carbodiimide, which activates chemical crosslinking. The level of crosslinking is preferably 0.01% to 50%, and more preferably 0.1% to 10%.

B. Additives for Use in Building PEMUs

The PEMUs of the present invention may be built by incorporating additives in the polyelectrolyte solutions which affect the thin film mechanical properties.

Optionally, the polyelectrolyte solutions may comprise one or more "salts." A "salt" is defined as a soluble, ionic, inorganic compound that dissociates to stable ions (e.g., sodium chloride). A salt is included in the polyelectrolyte solutions to control the thickness of the adsorbed layers. More specifically, including a salt increases the thickness of the adsorbed polyelectrolyte layer. In general, increasing the salt concentration increases the thickness of the layer for a given polyelectrolyte concentration and contact time. This phenomenon is limited, however, by the fact that upon reaching a sufficient salt concentration, multilayers tend to dissociate. Typically, the amount of salt added to the polyelectrolyte solution is about 10% by weight or less.

Both dip coating and spraying permit a wide variety of additives to be incorporated into a film as it is formed. Additives that may be incorporated into polyelectrolyte multilayers include inorganic materials such as metallic oxide particles (e.g., silicon dioxide, aluminum oxide, titanium dioxide, iron oxide, zirconium oxide, and vanadium oxide) and clay minerals (e.g., hectorite, kaolin, laponite, montmorillonite, and attapulgite). These particles typically range in size from about 1 nanometer to about 10 micrometers. For example, nanoparticles of zirconium oxide added to a polyelectrolyte solution or complex solution tend to improve the abrasion resistance of the deposited film. See Rosidian et al., *Ionic Self-assembly of Ultra Hard $ZrO_2$/polymer Nanocomposite Films*, Advanced Materials 10, 1087-1091 (1998).

Other additives include carbon fibers and carbon nanotubes (having a diameter less than 100 nanometer and an aspect ratio (length to width) of at least 10:1). Optionally, charged Teflon™ particles may be incorporated into the thin films. Typically, Teflon™ particles are charge neutral, but surfactants may be added onto the surface of the particles to impart a charge which may be positive or negative depending upon the surfactant employed. Particle additives are added to the polyelectrolyte solutions, or are layered between polyelectrolyte layers in separate coating steps. Optionally, the polymer film further comprises agents known to promote cell growth, i.e., growth factors, and other cell nutrients. Optionally, the film further comprises agents known to inhibit cell growth, i.e., paclitaxel or sirolimus.

C. Deposition Methods and Substrates

While this invention employs polyelectrolyte complex thin films, a preferred method of depositing said complex is by the alternating layer-by-layer deposition method. The preferred method of alternating exposure of the substrate or material to be coated is by alternate immersion in polyelectrolyte solutions, or alternate spraying of polyelectrolyte solutions. The alternating polyelectrolyte layering method, however, does not generally result in a layered morphology of the polymers with the film. Rather, the polymeric components interdiffuse and mix on a molecular level upon incorporation into the thin film. See Lösche et al., *Macromolecules* 31, 8893 (1998). Thus, the polymeric components form a true molecular blend, referred to as a "polyelectrolyte complex," with intimate contact between polymers driven by the multiple electrostatic complexation between positive and negative polymer segments. The complexed polyelectrolytes within the PEMU film have similar morphology to a polyelectrolyte complex formed by mixing solutions of positive and negative polyelectrolyte. It is also known that although there is extensive intermingling of neighboring layers over a range of 4-6 nominal layers, it is possible to obtain actual layers of different composition, or strata, by interspersing several layers made from one pair of polyelectrolytes by several layers made from a different pair. See Lösche et al., *Macromolecules* 31, 8893 (1998). For example, if polymers A and C are positively charged and polymers B and D are negatively charged, about 3 or 4 pairs of A/B layers followed by about 3 or 4 pairs of A/D or C/D layers will produce two strata of distinct composition. The preferred concentration for solutions comprising polyelectrolytes to be deposited is in the range 0.01 weight % to 10 weight %, and preferably 0.1 weight % to 1 weight %.

Alternatively, the thin film coating may be applied to a surface using a pre-formed polyelectrolyte complex. See Michaels, *Polyelectrolyte Complexes*, Ind. Eng. Chem. 57, 32-40 (1965) and Michaels (U.S. Pat. No. 3,467,604). This is accomplished by mixing the oppositely-charged polyelectrolytes to form a polyelectrolyte complex precipitate which is then dissolved or re-suspended in a suitable solvent/liquid to form a polyelectrolyte complex solution/dispersion. The polyelectrolyte complex solution/dispersion is then applied to the substrate surface and the solvent/liquid is evaporated, leaving behind a film comprising the polyelectrolyte complex. To aid in dissolution or dispersion of the complex, both a salt, such as sodium bromide, and an organic solvent, such as acetone is optionally added to the solution comprising the precipitated complex. It is known that the material obtained by layering two polyelectrolytes is substantially the same composition as material obtained by mixing and precipitating said polymers to form a polyelectrolyte complex.

In one embodiment of this invention, the polyelectrolyte complex is formed on a polymer or plastic surface. Polyelectrolyte complexes, especially those formed by the layer-by-layer alternating deposition technique, are known by those skilled in the art to adhere to plastic materials. For example, Chen and McCarthy (*Macromolecules*, 30, 78 (1997) describe the layer-by-layer deposition of polyelectrolyte complex on poly(ethylene terephthalate). Even fluorinated polymers, such as Dupont's Teflon™, are known to be coated by polyelectrolyte complex using the layer-by-layer technique (see Hsieh et al. *Macromolecules,* 30, 8453 (1997). Barker et al. (*Anal. Chem.,* 72, 5925 (2000)) (See also Locascio et al. U.S. Pat. Pub. No. 2002/0053514) have disclosed the layer-by-layer deposition of polyelectrolytes on plastic microfluidic channels. Thus, preferred plastic substrates on which polyelectrolyte complex films may be formed include polycarbonate, poly(methyl methacrylate), polystyrene, poly(ethylene terephthalate), polysulfone, or polyamide, with the proviso that solvents used to process the fluorinated polyelectrolyte complex thin film does not attack the substrate on which the thin film of complex is being formed.

For fast throughput and coating of surfaces, one method of applying the polyelectrolyte complex is by spraying of a surface. Spraying is especially preferred when applying the coating to large areas using alternating exposure of oppositely-charged polyelectrolyte solutions. Spraying alternating oppositely-charged polyelectrolyte solutions has several advantages over the Michaels coating and evaporation method, including: improved control over film thickness especially the ability to make extremely thin films (e.g., less than about 1 μm), and enhanced uniformity of film thickness especially over uneven surfaces and contours. The solutions may be sprayed onto a substrate by any applicable means (e.g., an atomizer, an aspirator, ultrasonic vapor generator, entrainment in compressed gas, or inkjet sprayer). In fact, a hand operated "plant mister" has been used to spray the polyelectrolyte solutions. Typically, the droplet size in the spray is about 10 nm to about 1 mm in diameter. Preferably, the droplet size is about 10 μm to 100 μm in diameter. The coverage of the spray is typically about 0.001 to 1 $mL/cm^2$, and preferably about 0.01 to 0.1 $mL/cm^2$.

In order to create a pattern of polyelectrolyte on a surface, spraying is preferably done though a mask which defines the pattern. Preferably, spraying through a mask is performed with a fine spray, such as that produced by ultrasonic vaporization. The mask is preferably placed on or near the surface to be coated. Many patterns of different levels of complexity are possible. Preferred dimensions for features on the mask range from about 10 micrometers to several centimeters.

It is known to those skilled in the art that fluorinated groups, especially chains of fluorinated hydrocarbons, cause aggregation, especially in aqueous solution. A system comprising aggregates as small particles dispersed in a solvent is known as a dispersion, or a suspension. A suspension of particles that are small enough such that they do not settle out is known as a colloid. Colloids in aqueous solution are often stabilized against aggregation into larger particles by having a surface charge. The surface charge can be derived directly from the material forming the colloid, or it can be maintained by the adsorption of a surface active agent, or surfactant. Charged surfactants stabilize suspensions by causing the surface of the particles to have the same charge and therefore repel each other. Neutral surfactants rely on steric interactions (repulsions) to prevent aggregation of suspended particles. In one embodiment of this invention, at least one of the fluorinated polymers is dispersed as a quasi-stable suspension in a solvent, and said suspensions are employed in the multilayering process. Preferably, the solvent comprising such suspensions comprises water. The particle size of the suspension is preferably less than about one micrometer, and more preferably less than about 100 nanometers. Preferably the particles comprising said suspension or dispersion bear a net surface charge.

Preferred suspensions comprise fluorinated polymers comprising charged repeat units. Other preferred suspensions comprise telomerized fluoropolymers, including those produced by Asahi Glass, Atochem, Daikin, such as Daikin 3310 or 3311, Dupont, such as Dupont Tufcoat (Anionic), and Clariant, such as the NUVA fluoropolymers, such as NUVA CPA, NUVA 5006, and Peach State Labs, such as Myafax WS.

It is also known to those skilled in the art that fluoropolymers may be dissolved or dispersed in supercritical carbon dioxide, $CO_2$. The dielectric constant of supercritical $CO_2$ is low and matches that of fluorinated hydrocarbons including fluorinated monomers, which may be polymerized to yield fluorinated polymers in supercritical $CO_2$ (see DeYong et al. Chapter 13, in *Fluoropolymers 1, Synthesis*, Hougham et al., Eds., Kluwer, New York, 1999). It is further known that fluoropolymers are swelled or dissolved in supercritical $CO_2$. Accordingly, in one embodiment of this invention, the fluorinated polyelectrolytes are applied by spraying them from solutions or suspensions in supercritical $CO_2$. Such application may proceed with simultaneous or sequential spraying of positive and negative fluorinated polyelectrolytes using different reservoirs for each polymer. The preferred concentration of fluorinated polyelectrolyte is 0.1 weight % to 10 weight %. Optionally, a small volume fraction of organic solvent such as ethanol or methanol may be added to the supercritical $CO_2$ to improve the dispersion of said fluorinated polyelectrolytes.

In a further embodiment of this invention, a suspension of a polyelectrolyte complex comprising at least one negative fluorinated polyelectrolyte and at least one positive fluorinated polyelectrolytes are sprayed onto a surface from supercritical $CO_2$.

The duration in which the polyelectrolyte solution is typically in contact with the surface it is sprayed upon (i.e., the contact time) varies from a couple of seconds to several minutes to achieve a maximum, or steady-state, thickness. The contact duration is selected based on the desired relationship between throughput (i.e., the rate at which alternating layers are created) and layer thickness. Specifically, decreasing the contact duration increases throughput and decreases layer thickness whereas increasing the duration decreases throughput and increases thickness. Preferably, the contact time is selected to maximize the throughput of layers that have a satisfactory thickness and are uniform across the surface.

Other preferred methods of depositing the polyelectrolyte solutions and/or polyelectrolyte complex include casting, dip coating, and doctor blading. Particularly preferred methods are dip coating and spraying.

Optionally, rinsing may be employed to remove nonadsorbed polyelectrolyte between the application of each polyelectrolyte solution. The rinsing liquid comprises an appropriate solvent (e.g., water or organic solvent such as alcohol). For water-soluble polyelectrolytes the preferred solvent is water. If the solvent is water, the rinsing liquid may also comprise an organic modifier (e.g., ethanol, methanol, or propanol). The concentration of organic modifier can be as high as less than 100 percent by weight of the rinsing liquid, but is preferably less than about 50 percent by weight. The rinsing liquid may also comprise a salt (e.g., sodium chloride) which is soluble in the solvent and the organic modifier, if included in the rinsing liquid. The concentration of salt is preferably below about 10 percent by weight of the rinsing liquid. It should be noted that as the concentration of organic modifier increases the maximum solubility concentration of salt decreases. The rinsing liquid, however, should not comprise a polyelectrolyte. The rinsing step may be accomplished by any appropriate means (e.g., flushing, dipping, or spraying). For spray rinsing, the amount of waste is preferably reduced by recycling the polymer solutions removed from the surface. Optionally, prior to depositing the second through $n^{th}$ layer of sprayed oppositely charged polyelectrolyte solution, the surface of the multilayer structure may be dried.

When performing multilayering by dipping, in order to avoid precipitation through cross-contamination, at least one of the rinse steps preferably employs a solvent which mixes with the solvents in which the polyelectrolytes are dissolved/dispersed.

Particles with diameters ranging from nanometers to millimeters may also be coated with polyelectrolyte complex. If the alternate layering method is used, it is not practical to coat particles individually. Neither is the spray method practical, unless particles are larger than about 100 μm. Instead, batches of particles are alternately immersed in coating solutions, with intervening rinse, as detailed by Caruso and Sukhorukov, Chapter 12 in "Multilayer Thin Films", G. Decher and J. B. Schlenoff, Eds., Wiley-VCH, Weinheim, 2003. See also Donath et al., U.S. Pat. Pub. No. 2003/0219384.

In a preferred embodiment of this invention, the tissue engineering aspects of this invention are promoted by coating complex objects with the polyelectrolyte complex films of this invention. Assemblies of cells are then allowed to grow into functional tissues within this complex object. In one embodiment of this invention, the complex object is a porous "scaffold," or structural support. Preferably, the scaffold provides a three dimensional cell growth environment, in which cells are in close proximity such that the cells may self-assemble. See S. Levenberg, et al., "Embryonic Stem Cells in Tissue Engineering," to be submitted to HANDBOOK OF EMBRYONIC STEM CELLS, Eds. D. Melton, et al. The entire scaffold is on the order of several millimeters in each dimension. A scaffold may be, for example, about 5 mm, about 8 mm, and even up to about 12 mm in each dimension. The scaffold is preferably porous, having pore diameters as small as about 10 um to pores as large as about 1000 um in diameter, more preferably between about 100 um to about 600 um. The pore void volume in the scaffold may be about 40% to about 90% of the volume of the entire scaffold. See Valentini et al., U.S. Pat. No. 5,939,323. Said scaffold is typically a porous mesh or foam or collection of bundled fibers. Said scaffold may be biodegradable or nonbiodegradable. The function of the scaffold is to direct the growth of cells from surrounding tissue or the growth of cells seeded within the porous structure of the scaffold. In the cases where a temporary role for the scaffold is desired, biodegradable scaffold materials are preferred. Polymer scaffolds are well known to those skilled in the art, as detailed in R. C. Thomson et al., Chapter 21 in "Principles of Tissue Engineering," $2^{nd}$ Ed., Eds. R. P. Lanza, R. Langer, J. Vacanti, Academic Press, San Diego, 2000.

Advantageously, a polyelectrolyte complex thin film coating on a scaffold material represents a small fraction of the total material on which cells grow. For example, a polyelectrolyte complex thin film might have a thickness of 0.01 micrometer, whereas the article or scaffold on which said thin film is deposited might have dimensions of hundreds of micrometers or even millimeters.

Preferred synthetic polymers for making biodegradable articles, including scaffolds for in vitro and in vivo tissue cultures, known to those skilled in the art (see A. Atala et. al "Synthetic Biodegradable Polymer Scaffolds," Birkhauser Publishers, Boston, 1997, for example), include poly(glycolic acid), poly(lactic acid), poly(β-hydroxybutyrate), poly(caprolactone), polyphosphazenes, poly(propylene fumarate), polyarylates, polyethylene glycol, and copolymers made from these examples. Preferred biodegradable polymers from biological sources include collagen, glycosaminoglycans, hyaluronic acid, chitosan, polyhydroxyalkanoates, alginates, and modified polysaccharides, such as cellulose, starch, and chitin.

Scaffold coated entirely with polyelectrolyte complex comprising a surface layer of fluorinated polyelectrolyte is hydrophobic and therefore difficult to wet. Preferred scaffolds comprising thin films of polyelectrolyte complex comprising fluorinated polymer also comprise areas coated with hydrophilic polyelectrolyte complexes, such as polyelectrolyte complexes comprising polycarboxylic acid, or a copolymer of carboxylic acid repeat unit, and zwitterionic repeat unit. The preferred scaffold is made by intermingling individual fibers of biodegradable polymer previously modified with either polyelectrolyte complex thin films comprising fluorinated (hydrophobic) or hydrophilic repeat units.

Optionally, said polymer scaffold material also comprises inorganic material known to those skilled in the art to impart mechanical strength and/or rigidity to the scaffold, such as hydroxyapatite and calcium carbonate. Preferably, said inorganic material comprises hydroxyapatite particles, preferably with an aspect ratio of greater than about 5:1.

Optionally, said polymer scaffold further comprises agents known to promote growth, i.e., growth factors, and other cell nutrients. Optionally, the polymer scaffold may comprise immobilized ligands such as RGD peptides and the adherent domain of fibronectin, to provide an anchor for cells.

A preferred scaffold for preparing layers of cultured cells is a porous film of polyelectrolyte complex described by Hiller et al. (see Nature Mat. 1, 59 (2002) and U.S. Pat. Pub. No. 2003/0215626). Such a film is created by preparing a polyelectrolyte thin film complex comprising weak acid or weak base units, then changing the state of charge of the weak acid or base in said thin film complex, which results in phase separations of polymeric constituents and porosity. For the purposes of this invention, such a porous material is rendered suitable for promoting cell growth by coating it with at least one layer of fluorinated polyelectrolyte.

In another embodiment of this invention, the complex object which supports growth of cells is a template. A preferred template is a tube, or a plurality of tubes. In a preferred mode of application of this invention, the external surface of a tube or fiber, preferably of diameter in the range about 1 micrometer to about 1 millimeter, is coated with the polyelectrolyte complex of this invention. Cells are then allowed to grow on this tube or fiber. Optionally, the tube comprises biodegradable material so that it partially or fully degrades over time, whether in vitro or in vivo. An alternative preferred mode of growth on tube templates is to coat the internal surface of a tube and to allow cells to grow on the internal surface of said tube. Optionally, both the internal and external surface of a tube is coated with the polyelectrolyte complexes of this invention. Preferred materials for said tubes or fibers are of the type known to those skilled in the art, and include poly(glycolic acid), poly(lactic acid), poly(β-hydroxybutyrate), poly(caprolactone), polyphosphazenes and copolymers made from these examples, as well as collagen, glycosaminoglycans, hyaluronic acid, chitosan, polyhydroxyalkanoates, and modified polysaccharides, such as cellulose, starch, and chitin.

In yet another embodiment of the present invention, the polyelectrolyte complex is a coating or layer on a substrate or substratum and may be deposited according to any appropriate method (see, e.g., supra, as a multilayer or as a pre-formed polyelectrolyte complex). The substrate may be non-porous or porous and may be comprised of many types of materials that are well known in the art such as polymers, metals, and ceramics. The surface of polymeric support materials may be positively charged by comprising tetraalkyl ammonium groups, negatively charged by comprising sulfonate groups, or neutral. In another embodiment the substratum is porous and comprises a material selected from the group consisting of polypropylene, nylon, polytetrafluoroethylene, glass, and alumina (all of which are known to those of skill in the art). Typically, the average size of the pores is between about 100 nm and about 10 μm and the degree of porosity is between about 0.1 and about 60%. "Degree of porosity" refers to the volume % of the material that is occupied by pores. Advantageously, when the fluorinated polyelectrolytes of the present invention are applied to a porous substrate, the polyelectrolytes achieve a high degree of penetration into the substrate's pores. For example, a first polyelectrolyte solution comprising a charged fluorinated polyelectrolyte may be applied to a porous substrate and the solution allowed to penetrate the pores. A second polyelectrolyte solution comprising a charged fluorinated polyelectrolyte having a charge opposite to that of the first polyelectrolyte solution may then be applied to the porous substrate. The oppositely charged fluorinated polyelectrolytes may then form an interpenetrating network of complexed fluorinated polyelectrolytes which is insoluble, which is resilient, and which will not migrate once applied to the porous substrate.

In another embodiment the polyelectrolyte complex is a free, or isolated, membrane. Typically, an isolated membrane comprising a polyelectrolyte complex is formed by depositing the complex on a support and then dissolving the support. For example, a cellulose acetate support may be dissolved with acetone to remove it from a multilayer comprising charged particles and polymers. See Mamedov et al., *Langmuir* 16, 5530 (2000). This process typically has characteristics that are often considered to be drawbacks. For example, it may be slow, it typically requires disposal of organic solvents, it destroys the substratum, it may be difficult or impossible to employ on a multilayer membrane which does not contain charged particles, and it may denature, or deactivate, biologically-derived species (e.g., enzymes) incorporated within the membrane.

Alternatively, isolated membranes may be produced by using a release stratum that has a composition that is different from the remainder of the membrane, the release stratum is designed to decompose, dissociate, or become weakly associated under certain conditions (e.g., a change in salt concentration, pH, and/or temperature) thereby freeing the membrane from a substratum. This approach was set forth in U.S. Prov. App. Ser. No. 60/284,723, PCT App. No. PCT/US02/11917, and U.S. application Ser. No. 10/475,236 which are hereby incorporated by reference in their entirety for all purposes. These disclose a releasable membrane structure for producing a free membrane comprising a substratum or support and a release stratum deposited on the substratum. In the present invention, a membrane stratum comprising the polyelectrolyte complex of this invention, such as fluorinated polyelectrolytes, or polyelectrolytes comprising zwitterion repeat units, is deposited on the release stratum. Each release stratum comprises at least two oppositely-charged polyelectrolytes and is preferably a sequence of alternating oppositely-charged polyelectrolytes applied as layers. Selective decomposition of the oppositely-charged polyelectrolytes of the release stratum affords controlled separation of high quality free membranes. Examples of release stratum polyelectrolytes and dissociation stimuli include: PSS/PDADMA released by a NaCl solution about 3.5 M; PAA/PDADMA released by a NaCl solution about 0.6 M; and PSS/PDADMA-co-PAA released by a solution having a pH 6. Thus, depending on the desired polyelectrolyte free membrane, the appropriate oppositely-charged polyelectrolytes may be selected to create a release stratum that decomposes, dissociates, or becomes weakly associated under conditions which do not negatively impact the integrity of the free membrane. A preferred release stratum is a multilayer of PDADMA-co-PAA random copolymer with a PAA content of between 20 and 60 mole % (based on the polymer repeat unit) layered with PSS under conditions of solution and rinse pH of less than about 4. The preferred release stimulus for this stratum is exposure to solution pH above about 5.

In one embodiment of this invention, a free membrane is created with a hydrophobic stratum on one side and a hydrophilic stratum the other side. Preferably the hydrophobic stratum comprises fluorinated polyelectrolyte. Preferably the hydrophilic stratum comprises polyacrylic acid, and, more preferably, the hydrophilic stratum comprises a copolymer of acrylic acid and a zwitterion, where the zwitterion preferably comprises between 10 and 80 mole % of said copolymers. Preferably the zwitterion repeat unit is 3-[2-(acrylamido)-ethyldimethyl ammonio]propane sulfonate, AEDAPS. Preferably, both sides of the membrane bear the same charge, so that there will not be a tendency for the membrane to self-associate.

A free membrane bearing such a fluorinated hydrophobic surface on one side and a hydrophilic surface on the other side is used advantageously where cell adhesion, growth, and proliferation is required on one side of the membrane but not on the other side. Thus, a preferred application of said membrane is as a wound dressing. In a similar preferred application, a film comprising synthetic polymers known to those skilled in the art, such as polyvinyl chloride, polyurethane, polysiloxanes, and other elastic polymers is advantageously coated with a thin film of polyelectrolyte complex comprising fluorinated polyelectrolyte. Said coated synthetic polyelectrolyte film is also preferably applied as a wound dressing. The membrane surface on which the thin film of polyelectrolyte complex is coated is preferably in contact with the wound area to encourage cell and tissue growth and healing.

In yet another embodiment of this invention, an area on which cells are to adhere and grow is defined by microcontact printing of fluorinated polyelectrolyte to a surface. Microcontact printing is a method, known to those skilled in the art, whereby a patterned stamp is "inked" with a material to be transferred to a surface (for a description, see S. Takayama et al, Chapter 18 in "Principles of Tissue Engineering," $2^{nd}$ Ed., Eds. R. P. Lanza, R. Langer, J. Vacanti, Academic Press, San Diego, 2000). Small molecules and large molecules may be transferred efficiently from the stamp features, faithfully reproducing the stamp pattern, which may have dimensions down to the micrometer range. For microcontact printing, the fluorinated polyelectrolyte is preferably applied to the surface of the stamp with a cotton swab, allowed to dry, and then pressed on the surface to be patterned. The width of the area on which cells attach and grow is determined by the width of the raised areas of the stamp features, from which cytophilic polymer is patterned. For oriented cell growth it is preferable to maintain a sufficiently narrow width of cytophilic material. Preferred line widths for oriented cell growth are on the order of the cell width. Preferred line widths for smooth muscle cells are from 5 to 50 micrometers. For dense packing of oriented cell growth, the cytophilic areas on the surface are preferably a plurality of closely-spaced parallel lines.

A preferred mode of pattern formation for patterned cell growth is to employ a stamp inked with fluorinated polyelectrolyte and to stamp said polyelectrolyte on the surface of a polyelectrolyte thin film, preferably prepared by the polyelectrolyte multilayer technique, comprising at least one surface layer of polyelectrolyte comprising zwitterion repeat units. This operation produces a pattern of high hydrophobicity contrast. Cells are then permitted to attach and grow on the areas comprising fluorinated polyelectrolyte on the surface (from the stamp) and are substantially excluded from areas comprising the hydrophilic zwitterionic polyelectrolyte on the surface. Preferred compositions for patterned growth are in accord with preferred compositions listed above for encouraging or preventing cell adhesion and growth on surfaces. This strategy of contrasting hydrophobic and hydrophilic areas on a surface leads to highly localized and directed growth of cells, as shown in the examples.

In another preferred mode of pattern formation, a patterned stamp is inked with fluorinated polyelectrolyte and said fluorinated polyelectrolyte is then stamped onto the surface of a thin film of polyelectrolyte complex comprising a zwitterionic repeat unit. The pattern is then immersed into a solution comprising at least one protein. The protein adsorbs to the fluorinated areas and is repelled from the zwitterionic areas. The patterned protein is then preferably employed as a substrate for cell growth. Preferably, proteins known to enhance the adhesion of cells to surfaces, more preferably fibrinogen and/or fibronectin, are patterned in this manner.

The following examples further illustrate the invention. The above described polyelectrolytes and additives were used for building thin films of a variety of compositions on substrates. The thin films, solutions, and additives were modified in various ways as shown in the examples, and the effects of those modifications on the inhibition/enhancement of cell adhesion, growth, and differentiation were monitored. While the number of possible combinations is immense, the goal was to make some broad deductions concerning the role of film composition and modification in the adhesion of cells. The examples are illustrative and not meant to be limiting.

For clarity, the following shorthand for multilayers is used: $(A/B)_x$ where A is the starting polyelectrolyte contacting the substrate, B is the terminating polyelectrolyte in contact with subsequent cell solutions and x is the number of layer pairs. In $(A/B)_xA$, A would be the terminating polymer. Salt, MY (cation M and anion Y), has an important role in the buildup process and is represented by $(A/B)_x@c$ MY, where c is the molarity of the salt (MY) in the polymer solution. The pH can be included in the nomenclature especially when using pH dependent PEMUs. For example, $(PAH/PAA)_2 @0.25$ M NaCl @pH 7.4, represent two pairs of PAH/PAA built at 0.25 M NaCl and a pH of 7.4.

EXAMPLE 1

Material Used to Build PEMUs and Characterization Methods

Materials. 1,3 propane sultone (PS) and acrylic acid were obtained from Aldrich. 2-(acrylamido)-ethyl dimethyl amine (AEDA) was obtained from Monomer-Polymer & Dajac Inc. Poly(styrenesulfonic acid), PSS (molecular weight, MW $7.3\times10^4$, $M_w/M_n=1.06$) poly(diallyldimethylammonium chloride), PDADMAC (MW $3.7\times10^5$, $M_w/M_n=2.1$), poly(allylamine hydrochloride), PAH (MW ~$7\times10^4$) and poly(acrylic acid), PAA (MW ~$2.4\times10^5$) were used as received from Aldrich. Poly(N-methyl-2-vinyl pyridinium iodide-block-ethylene oxide), PM2VP-b-PEO (PM2VP block 86% quarternized, respective block molecular weights 56,500:5900 $M_w/M_n=1.08$), poly(methacrylic acid-block-ethylene oxide), PMA-b-PEO (respective block molecular weights 41,000:30,700 $M_w/M_n=1.5$) and poly(4-vinyl pyridine), P4VP (MW ~$5\times10^4$) were from Polymer Source Inc.

Nafion® was purchased from Aldrich and used as 2.5 wt. % solution in ethanol:methanol 50:50 vol/vol for stamping. All polymer, monomer, and buffer solutions were prepared using 18 MΩ water (except fluorinated polymers).

Polyelectrolyte Multilayers on Glass Cover Slips. Glass cover slips (cover glass, No. 1½, 22 mm sq., Corning) were cleaned in 70% $H_2SO_4$ (conc.)/30% $H_2O_{2(aq)}$ ("piranha:" caution, piranha is a strong oxidizer and should not be stored in closed containers) then in hot $H_2O_2$/ammonia/water, 1:1:7 vol/vol, rinsed in water and blown dry with a stream of nitrogen. Polymer solution concentrations were 10 mM (with respect to the monomer repeat unit) in 0.25 M sodium chloride salt (NaCl, Fisher) except for Nafion® which was 0.25 wt. % solution in ethanol:methanol 50:50 vol/vol and PFPVP which was 2 mM. Sequential adsorption of polyelectrolytes on cover slips was performed by hand dipping, where the exposure time for the two polymers was 10 minutes with three rinses of fresh distilled water, 1 minute each, between.

Film Thickness. The film thickness was determined using a Gaertner Scientific L116S autogain ellipsometer with 632.8 nm radiation at 70° incident angle. A refractive index of 1.54 was employed for the multilayer film. For fluorinated polymers, a refractive index of 1.35 was used. Thicknesses are quoted as "dry" thickness.

Contact Angle Measurements. Water contact angles measurements were recorded using a contact angle goniometer (Ramé-Hart, Inc.) with the sessile drop technique. Measurements were done at 5 different locations of the sample and averaged (RSD 10%). The volume of the drop was maintained at 10 µL.

Polymer Stamping. Polymer-on-polymer stamping (POPS), as described by Jiang and Hammond (*Langmuir*, 16, 8501 (2000)), was done with a poly(dimethylsiloxane) stamp, (PDMS), that had defined parallel channels. In this technique, the surface of a patterned PDMS was inked by applying 2.5 wt % Nafion® using a cotton swab, and drying with a nitrogen stream. The patterned side of the stamp was brought in contact with the multilayer surface for 10 minutes. The surface was characterized with a KLA-Tencor P15 Surface Profiler (KLA-Tencor).

Cell Culture. The A7r5 rat aortic smooth muscle cells (American Type Culture Collection) were cultured in Dulbecco's modified Eagle medium high glucose supplemented with 10% fetal bovine serum, 100 units $mL^{-1}$ Penicillin G, 100 µg $mL^{-1}$ Streptomycin and 10 µg $mL^{-1}$ Gentamicin. Cells were plated onto 75 $mm^2$ culture flasks and maintained at 37° C. in a humidified atmosphere with 5% $CO_2$ in air. Cells were fed once per week and passaged when they reached 85% confluency. Cells were released from culture flasks using a trypsin and ethylenediamine tetraacetic acid (EDTA) solution in Hanks buffered salt solution (HBSS).

Microscopy. Equal numbers (~$1\times10^4$ cell $mL^{-1}$) of A7r5 cells were plated onto bare or polyelectrolyte coated glass cover slips in 6-well dishes and grown for 30-48 hours to allow cell attachment before imaging. Live cell phase images were obtained using a Zeiss Axiovert-35 microscope equipped with a NEC Ti-24A CCD camera and Metamorph Imaging Software. For staining, cells were washed once with cold phosphate buffered saline pH 7.4 (PBS) and then fixed with ice cold acetone for 1 min. Following 3 washes with PBS, the cells were blocked with 1% bovine serum albumin (BSA) in PBS for 30 minutes. The cells were stained using 1 unit of Alexa Fluor® 488 phalloidin (Molecular Probes, Inc.) in PBS for 20 minutes at room temperature. The cells were washed 3 times in PBS and the cover slips were mounted in Vectashield (Vector Laboratories Inc.) mounting medium containing 1.5 µg $mL^{-1}$ 4',6-diamidino-2-phenylindole (DAPI). Stained cells were observed with a Nikon Microphoto-FX microscope and imaged using a Zeiss color Axiocam.

EXAMPLE 2

Polyelectrolyte Synthesis

3-[2-(acrylamido)-ethyl dimethylammonio]propane sulfonate, AEDAPS

The zwitterionic monomer was made from 2-(acrylamido)-ethyldimethyl amine (AEDA) and PS. 200 ppm methyl ethyl hydroquinone inhibitor was removed from AA and AEDA by passing the monomer through a column of DTR silica column (Scientific Polymer Products Inc.). 1.0 equivalent of AEDA (1.42 g, 10 mmol) was dissolved in 28 mL of propylene carbonate (PC). 1.1 equivalent of PS (1.34 g, 10.1 mmol) was added to the reaction mixture. The reaction was stirred at 45° C. for 1 hr. The product, 3-[2-(acrylamido)-ethyldimethyl ammonio]propane sulfonate, AEDAPS, precipitated and was washed with petroleum ether with a product yield of 60%. $^1$H NMR (300 MHz, DMSO): δ 8.45 (bs, 1H), 6.15 (m, 2H), 5.55 (m, 1H), 3.21 (m, 2H), 3.32-3.59 (m, 6H), 3.06 (s, 6H), 2.47 (t, 2H). FTIR: N—H, 3270 cm$^{-1}$ (m); C=C—H 3037 cm$^{-1}$, aliphatic C—H, 2964 cm$^{-1}$; amide C=O, 1668 cm$^{-1}$ (s); and 1545 cm$^{-1}$ (s); C=C stretch 1628 cm$^{-1}$; S—O, 1200 cm$^{-1}$ (s).

PAA-co-PAEDAPS Copolymer.

The copolymer was made from AEDAPS and AA via free radical polymerization. The monomer feed for AA:AEDAPS was 90:10 or 75:25 mole ratios. The monomers were dissolved in aqueous 0.5 M NaCl concentration to assist homogeneity of the copolymer. PAA-co-PAEDAPS (90:10 mol %) was made by copolymerizing 2.4 g, 33 mmol AA with 3.2 g, 12 mmol of AEDAPS. Similarly, for PAA-co-PAEDAPS (75: 25 mol %), 0.77 g, 11 mmol of AA and 4.27 g, 16 mmol were used. Total monomer concentration was 0.9 M in 30 mL of distilled water. Potassium persulfate, 7.2 mg (0.1 mol %), was then added to the mixture which was heated at 50° C. under argon and stirring for 120 h. The product was dialyzed against distilled water using 14,000 molecular-weight-cutoff dialysis tubing. Elemental analysis (E.A., Atlantic Microlab Inc.) for PAA-co-PAEDAPS (90:10 mol %) $(C_3H_4O_2)_{0.9}$-co-$(C_{10}H_{20}N_2O_4S)_{0.1}$. theory (found): C, 47.98% (46.75%); H, 6.14% (6.04%); N, 3.10% (2.30%); S, 3.51% (2.65%). E.A. for PAA-co-PAEDAPS (75:25 mole %), $(C_3H_4O_2)_{0.75}$-co-$(C_{10}H_{20}N_2O_4S)_{0.25}$. theory (found): C, 47.50% (45.41%); H, 6.66% (6.93%); N, 5.83% (5.38%); S, 6.66% (6.60%). The polymers were characterized using FTIR which confirmed the presence of both carbonyl stretch C=O (1725 cm$^{-1}$, AA and 1670 cm$^{-1}$ AEDAPS) and the appearance of sulfonate ($v_{SO_3-}$) stretch at ~1200 cm$^{-1}$.

P4VTDFOP-co-P4VP copolymer, "PFPVP".

1,1,1,2,2,3,3,4,4,5,5,6,6-tridecafluoro-8-iodooctane (TDFI, $C_8H_4F_{13}I$) was reacted with P4VP to give poly(4-vinyl-trideca-fluoro-octyl pyridinium iodide)-co-poly(4-vinyl pyridine). DMF and nitromethane, previously dried using molecular sieves, were used to dissolve the reactants. 1.0 equivalent (1.05 g, 10 mmol) of P4VP was dried at 110° C. for 4 h and then dissolved in a 50 mL 1:1 v/v dry mixture of DMF and nitromethane under stirring conditions for 72 hours at 50° C. 1.2 equivalents (5.7 g, 12 mmol) of TDFI was then added to the reaction mixture and left for 48 hours under inert atmosphere. The product was precipitated using ethyl acetate then washed with petroleum ether and dried under vacuum for 24 hours at 60° C. E.A for PFPVP, $(C_{15}H_{11}NF_{13}I)_{0.45}$-co-$(C_7H_7N)_{0.55}$. theory (found): 40.90 (40.95) % C, 3.39 (3.34) % H, 5.06 (5.11) % N, 29.46 (29.54) % F and 17.58 (17.48) % I. The elemental analysis results showed the polymer to be 45±3% quaternized with the fluorinating reagent. Experimental reaction yield was 90%. The polymer was characterized by FTIR spectroscopy and was identifiable by the distinctive C—F stretch in the 1200 cm$^{-1}$ region of the spectrum.

EXAMPLE 3

Building Up a PEMU Comprising a Zwitterionic Homopolymer

Zwitterionic polyelectrolytes comprise repeat units that bear a negative and a positive charge. Opposite charges on a repeat unit are in relatively close proximity and therefore have an opportunity to interact strongly. Because the zwitterion group is charge balanced (charge neutral) it does not require counterions when in solution.

Given that opposite charges on zwitterion polymer repeat units interact with each other, the question arises as to whether polyzwitterions would interact with other charged polymers. If there is no electrostatic or charge-pairing interaction between molecules, there is no driving force for intermolecular attraction and therefore no driving force for polyelectrolyte complexation, which is required for multilayer buildup.

An attempt was made to construct a multilayer from the zwitterionic polymer poly(N-propane sulfonate-2-vinyl pyridine), P2PSVP, and a negative or positive polyelectrolyte. For example, P2PSVP and PDADMA were employed for attempted multilayer buildup at pH 5. Under this condition, the multilayer did not build because the negative sulfonate on the P2PSVP interacted with the positive pyridinium on P2PSVP, an intramolecular interaction, rather than with the PDADMA repeat unit (intermolecular interaction). Similarly, multilayers could not be constructed from P2PSVP and PSS at near-neutral (pH 5-7) conditions because the PSS does not interact sufficiently with the pyridinium nitrogen on P2PSVP. However, if the pH is lowered below about pH 2, multilayers may be built from PSS and P2PSVP. At this low pH even the strongly acidic sulfonate groups on P2PSVP are protonated, leaving some of the pyridinium groups unpaired for intermolecular interactions. Multilayers constructed in this way and exposed to higher pH developed porosity and decomposed as a result of the changing internal charge within the multilayer.

Figure 1:
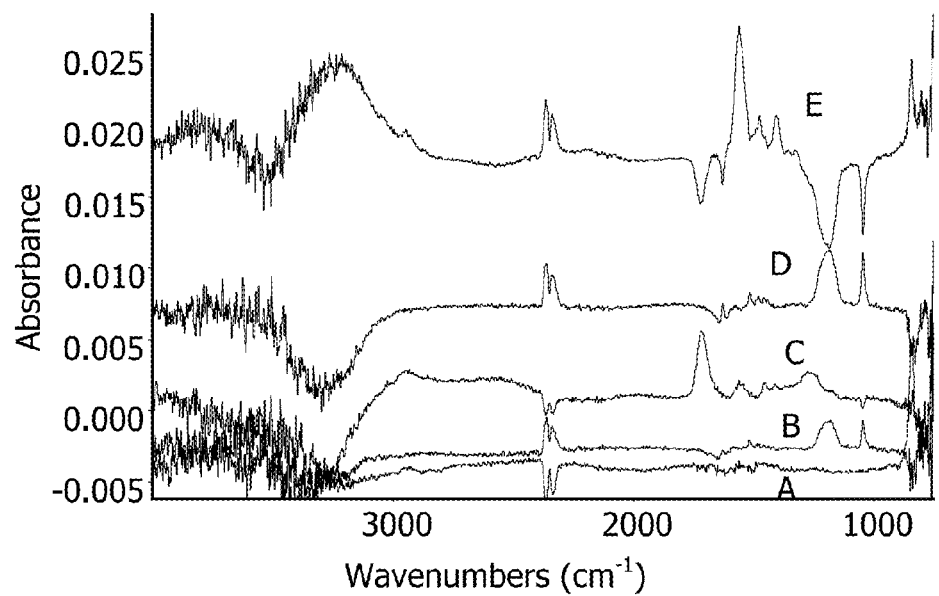
FIG. 1 is an ATR-FTIR spectrum showing the buildup of layers according to the method of Example 3. A corresponds to PDADMA, B corresponds to (PDADMA/P2PSVP), C corresponds to (PDADMA/P2PSVP/PAA), D corresponds to (PDADMA/P2PSVP/PAA/P2PSVP), E corresponds to (PDADMA/P2PSVP/PAA/P2PSVP/PDADMA). The negative peak in E indicates loss of the zwitterion P2PSVP.

In another example, PAA, PDADMA, and P2PSVP were employed to make a multilayer. ATR-FTIR was used to check for layer-by-layer buildup. ATR-FTIR monitored the buildup by looking at the characteristics peaks for the zwitterionic group (sulfonate stretch v~1033 cm$^{-1}$). The first layer was PDADMA (Curve A in FIG. 1), which is positively charged. The second layer was the P2PSVP, which was added successfully (Curve B in FIG. 1). The third layer was PAA, which showed the characteristic peaks for the C=O group in this polymer (Curve C in FIG. 1). The fourth layer was P2PSVP, which increased the signal for the sulfonate (Curve D in FIG. 1). The fifth layer was PDADMA, but negative peaks appearing in the P2PSVP region (Curve E in FIG. 1) indicated loss of all multilayer zwitterion, showing the P2PSVP was knocked off the surface and replaced by PDADMA. The loss of P2PSVP occurred every time PDADMA was added. Thus, it is clearly shown that polyelectrolyte bearing zwitterionic repeat units only do not form stable multilayers.

EXAMPLE 4

Figure 2:
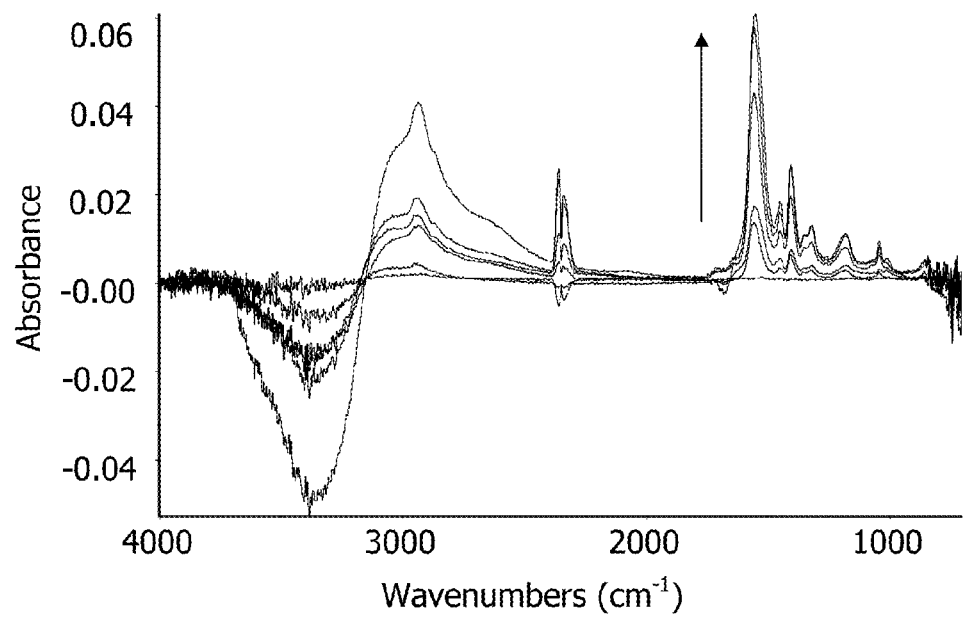
FIG. 2 is an ATR-FTIR spectrum showing the buildup of PAH/PAA-co-PAEDAPS PEMU according to the method of Example 4. The graph shows that layer-by-layer buildup is achievable using a copolymer, which was not the case when using the pure zwitterion polymer.
Figure 3:
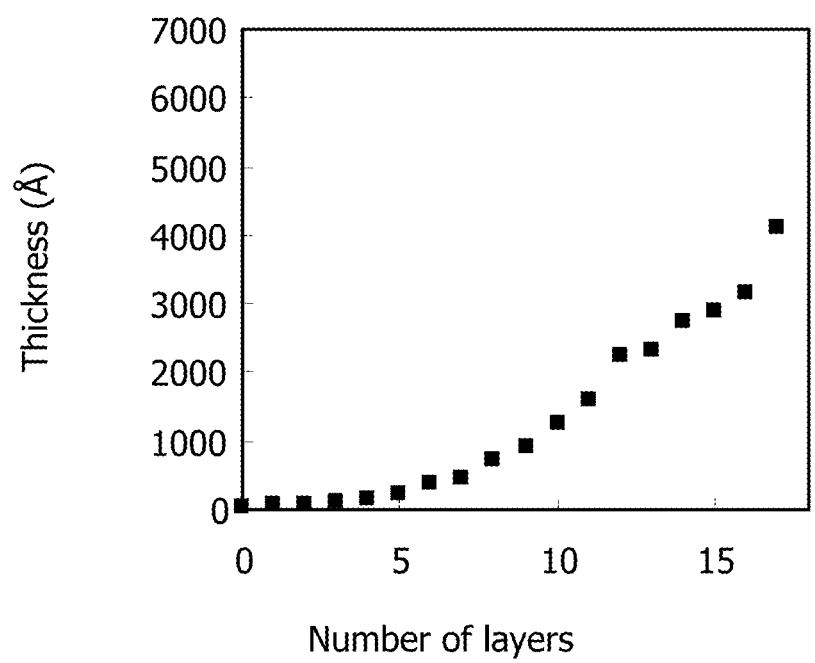
FIG. 3 is a graph of ellipsometric data showing thickness vs. number of layers for the buildup of poly(acrylic acid)-co-poly(3-[2-(acrylamido)-ethyldimethyl ammonio]propane sulfonate), PAA-co-PAEDAPS, and PAH according to the method of Example 4.

Building Up a PEMU Comprising a Zwitterionic Repeat Unit Co-polymerized with a Charged Repeat Unit By contrast, stable multilayers could be built with a copolymer comprising both zwitterion repeat units and charged repeat units, such as acrylic acid. FIG. 2 shows the FTIR of the characteristic zwitterion peaks in poly(acrylic acid)-co-poly(3-[2-(acrylamido)-ethyldimethyl ammonio] propane sulfonate), PAA-co-PAEDAPS, copolymer growing as a number of added layers, for a multilayer with the positive polyelectrolyte PAH. This clearly shows how the copolymer can be used in layer-by-layer buildup in contrary to the pure zwitterion polymer. FIG. 3 shows, by ellipsometry, the layer-by-layer buildup of a PEMU using PAA-co-PAEDAPS. Thus, it is shown that the net negative charge on the zwitterion-bearing polyelectrolyte copolymer stabilizes the multilayer by providing ion pairing interaction points with oppositely charged groups on other polyelectrolyte molecules.

EXAMPLE 5

Multilayer Thickness, Surface Charge, and Contact Angles

A selection of polyelectrolytes, summarized in Table VI, was employed to prepare various multilayers. Various contact angles were obtained, with the multilayers comprising a fluorinated polyelectrolyte as the outer layer having the highest contact angles (most hydrophobic).

TABLE VI

Thickness, Surface Charge and Contact Angles of Polyelectrolytes

| Multilayer | Thickness, Å | Surface Charge | Contact Angle |
|---|---|---|---|
| (PAH/PAA)$_2$ | 125 ± 6 | − | 5 ± 2° |
| (PAH/PAA)$_2$PAH | 181 ± 13 | + | 9 ± 2° |
| (PAH/PAA-co-PAEDAPS)$_2$ | 131 ± 3 | − | 10 ± 2° |
| (PAH/PAA-co-PAEDAPS)$_2$PAH | 175 ± 11 | + | 12 ± 2° |
| (P2VMP-b-PEO/PMA-b-PEO)$_2$ | 22 ± 4 | − | 15 ± 2° |
| (P2VMP-b-PEO/PMA-b-PEO)$_2$ P2VMP-b-PEO | 37 ± 2 | + | 20 ± 2° |
| (PDADMA/PSS)$_2$ | 38 ± 2 | − | 30 ± 3° |
| (PDADMA/PSS)$_2$PDADMA | 55 ± 4 | + | 55 ± 5° |
| (PFPVP/Nafion)$_2$ | 116 ± 6 | − | 100 ± 5° |
| (PFPVP/Nafion)$_2$PFPVP | 186 ± 11 | + | 100 ± 5° |

EXAMPLE 6

Growth of Smooth Muscle Cells on Polyelectrolyte Multilayers

Polyelectrolyte multilayers were fabricated to test the effect of both surface charge and surface hydrophobicity on smooth muscle cell attachment and spreading. Using a panel of negatively and positively charged surfaces with varying hydrophobicities, we developed both cell adhesive and cell repulsive surfaces. Both types of surfaces may be useful for different types of biological applications.

The A7r5 cells are vascular smooth muscle cells originally derived from rat aortic tissue. Smooth muscle cells were chosen considering the potential application of polyelectrolyte multilayers as coatings for stents, where the problem of restenosis is at least partially caused by the invasion of vascular smooth muscle cells onto implanted stents. A highly cell resistant surface would be of use as a coating for implantable devices. We found that the nature of the polyelectrolyte surface controls whether the cells become highly spread, non-motile, and contractile with prominent stress fiber-like actin structures or more rounded and highly motile with actin filament-rich lamellipodia and filopodia. These different morphology-motility states reflect those of the 'contractile' and 'synthetic' phenotypes of smooth muscle cells.

A sampling of polyelectrolyte surfaces were chosen to explore the effect of charge and the hydrophobicity of the surface on smooth muscle cell morphology and motility. Table VI (above, Example 5) shows the measured contact angle (a measure of hydrophobicity) and thickness of the surfaces tested.

A7r5 cells cultured on these layers exhibited graded responses with respect to hydrophobicity on both negatively and positively charged polyelectrolyte surfaces, with the negatively charged surfaces being more cell-resistant than the positively charged surfaces of comparable or greater hydrophobicity (FIG. 4). A7r5 cells cultured on Nafion® and PFPVP, which differ in their surface charges but are similar in hydrophobicity with contact angles of 100°, exhibit the flat and spread appearance of the smooth muscle cell 'contractile' phenotype. The effect of the charge difference between Nafion® and PFPVP appears to be minimal, as the cell shapes appear nearly identical on both surfaces (FIG. 4A, 4D). Although well spread, the cells cultured on PSS (FIG. 4B) display more edge 'ruffling' than those on Nafion®, suggesting that the PSS cells have a more dynamic intracellular organization than the Nafion® cells. The PDADMA surface (FIG. 4E) although more hydrophobic than the oppositely charged PSS (FIG. 4B) appears to be more cell resistant. Many of the cells plated on the PDADMA surface failed to attach at all and those that did appear to be very active with cellular processes extending out in all directions. A7r5 cells cultured on the most hydrophilic surfaces, PAA (5±2°, FIG. 4C) and PAH (9±2°, FIG. 4F), appear to be motile, with little spreading and multiple filopodia. PAH, the most hydrophilic positively charged surface tested, appears to be more cell resistant than PAA. The morphology and motility of these cells is similar to smooth muscle cells of the 'synthetic' phenotype.

Other studies have shown that the rigidity of a substrate can affect cell attachment and alter cell shape. In this investigation, cell morphology and motility depended more on the hydrophobicity and charge of the top polyelectrolyte layer than on the thickness of the layers (Table VI). The thickness of each layer reported here was measured when dry. It is known however, that PEMUs swell when wet, and layers may become spongy (except for fluorinated polymers which are very hydrophobic). Comparison of cells grown on layers of similar dry thickness (FIGS. 4, A and C, B and C, D and F) demonstrates a distinct lack of cell morphology dependence on surface thickness.

EXAMPLE 7

Smooth Muscle Cells on Copolymers Comprising Hydrophilic Units

Figure 5A:
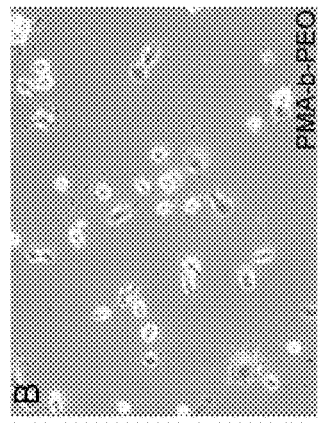
FIGS. 5A-5B are Axiocam phase images showing live A7r5 cells cultured on diblock polymers of (A)(PM2VP-b-PEO/PMA-b-PEO)$_2$PM2VP-b-PEO and (B)(PM2VP-b-PEO/PMA-b-PEO)$_2$ according to the method of Example 7. Right bottom tags represent outermost surface (scale bar=20 µm).
Figure 5B:
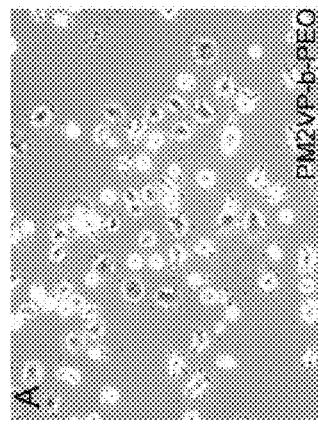

Multilayers of diblock polyelectrolyte polymers and copolymers produced some of the more pronounced and interesting effects on cell attachment (FIG. 5). PEMUs generated using two diblock polymers, each containing polyethylene oxide), PEO, with one containing PM2VP (poly(N- methyl-2-vinyl pyridinium iodide), FIG. 5A) and the other containing PMA (poly(methacrylic acid), FIG. 5B), also produced cell resistant hydrophilic surfaces. The cells cultured on these diblock polyelectrolytes were highly rounded, loosely attached, and had many filopodia. The positively charged diblock polymer (FIG. 5B) appeared to be more cell resistant than the negatively charged PMA surface (FIG. 5A).

EXAMPLE 8

Figure 6C:
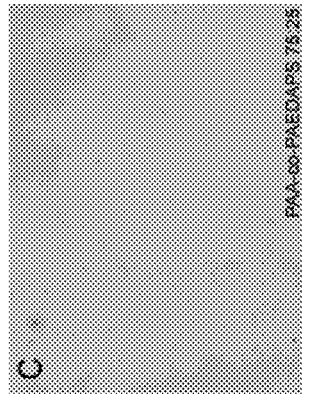
FIGS. 6A-6C are Axiocam phase images showing live A7r5 cells cultured on (A)(PAH/PAA)$_2$ (B) a 90:10 mol % copolymer mixture of PAA:AEDAPS, and (C) a 75:25 mol % copolymer mixture of PAA:AEDAPS according to the method of Example 8. Right bottom tags represent outermost surface (scale bar=20 μm).
Figure 6B:
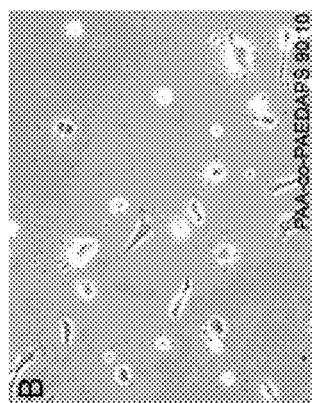
Figure 6A:
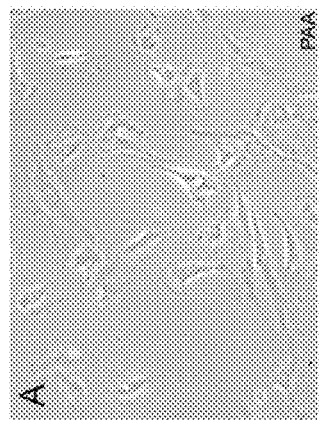

Cell Resistant Polyelectrolyte Complex Thin Films Comprising Zwitterionic Repeat Units Polymer surfaces with exposed zwitterion groups may mimic certain biological surfaces better than uniformly charged surfaces, because the head groups of three of the four major membrane phospholipids are zwitterions. The effect of a zwitterionic polymer surface on cell attachment was tested using copolymers containing AEDAPS, a zwitterion synthesized for this purpose, and acrylic acid, AA. As shown above (FIG. 4C), cells grown on the experimental control PAA surface were less spread than the more hydrophobic negatively charged surfaces, but cells adhered well and many displayed the prominent leading edge filopodia characteristic of motile cells (FIG. 6A). Our PAA-terminated $(PAH/PAA)_x$ multilayers appear to be more cell adhesive than those disclosed by Mendelson et al., (see *Biomacromolecules*, 4, 96 (2003)) possibly due to differences in the deposition conditions (pH), which maximized the proportion of PAA in their multilayers. Inclusion of AEDAPS in the copolymer made the surfaces even more cell resistant. On a 90:10 mol % PAA: PAEDAPS copolymer, the cells appeared to be much more loosely attached and have adopted a spiky appearance associated with active filopodia (FIG. 6B). Increasing the amount of the zwitterion in the copolymer to 75:25 mol % PAA: PAEDAPS yielded an extremely cell resistant surface. Indeed, the plated cells failed to attach and instead clumped together in non-adherent clusters that floated in the culture medium above the surface.

EXAMPLE 9

Patterning of a Multilayer Surface

Micropatterning of cultured cells has been used to investigate the effect of cell shape on various cell functions. Frequently, micropatterning of cells is accomplished using complex microfabrication techniques often requiring masking of patterned areas. The technique of polymer-on-polymer stamping makes the task of micropatterning polyelectrolyte multilayers a simpler process. For polymer-on-polymer stamping, a polyelectrolyte applied to a patterned stamp can be transferred to a polyelectrolyte multilayer surface of the same or opposite charge. In this investigation, we used a PDMS stamp in which 20 μm wide ridges were generated by cutting 80 μm wide grooves. These stamps were used to create cell-adhesive 20 μm wide lines of Nafion® on a cell resistant surface of 75:25 mol % PAA:PAEDAPS. When presented with this micropatterned surface, the A7r5 cells adhered only to the lines of Nafion®. Nuclear staining of cells on these surfaces revealed a regular distribution of elongate cells along the Nafion® lines (FIG. 7B). Phalloidin staining of the actin filaments in the cells revealed a distinct orientation along the Nafion® stripe, demonstrating that not only the cell shape can be guided by the stamped surface, but also the underlying organization of the cell cytoskeleton (FIG. 7A).

EXAMPLE 10

Modification of Cell Phenotype by Multilayer Surface

The peripheral regions of the PDMS stamp created a non-grooved Nafion® surface for a direct side-by-side comparison of cells growing on two different continuous layers of polyelectrolytes (FIG. 8). Analysis of cell behavior on these contrasting layers confirmed two important properties of the PEMUs. A single layer is sufficient to create a distinct cell phenotype, regardless of the composition of the underlying surface. Cells adhered and spread to the same degree on Nafion® stamped as a single layer on underlying surfaces with different properties of cell resistance—PAA:AEDAPS (FIG. 8A) or $(PAH/PAA)_2PAH$ (FIG. 8B)—or on a continuous layer of Nafion® overlying PFPVP (FIG. 4A).

This side-by-side analysis of cells on contrasting surfaces also revealed that the nature of the PEMU surface has a dramatic affect on the organization of the cell actin cytoskeleton. The cells associated with Nafion® stamped on PAH adopted very different cytoskeletal arrangements (FIG. 8C). Actin filaments in the cells on the PAH surface were located primarily in the spiky filopodia that are mediating the cell-surface interaction. This arrangement of actin filaments is consistent with the cells being primarily the non-muscle motile 'synthetic' phenotype.

In contrast, the actin filaments in the cells growing on the Nafion® surface are associated primarily with long stress fiber-like structures (FIG. 8C). It is likely that the cells growing on the Nafion® surface are in the 'contractile' phenotype and the ordered actin bundles are a part of the smooth muscle contractile apparatus. Clearly, the polyelectrolyte surface is capable of modulating the appearance of not only the cell adherence and spreading but also the underlying arrangement of the cellular cytoskeleton.

EXAMPLE 11

Controlling Platelet Adhesion

Development of more effective antifouling surfaces for blood contacting bioimplantable devices is of critical importance. Of particular interest is finding effective cell repellent surfaces to combat the problem of restenosis. Restenosis involves the progressive occlusion of blood flow caused by the buildup of cells and debris on an implanted stent. Adherence of platelets to implanted stents is one of the earliest steps leading to restenosis. We have developed and tested polyelectrolyte multilayer surfaces for their ability to resist platelet activation and adherence. Freshly isolated human platelets were washed extensively and incubated in an activated or unactivated state on polyelectrolyte coated coverslips for a period of sixty minutes at 37° C. Following the incubation period, the coverslips were gently washed, fixed, and stained using Alexa 488 labeled phalloidin to detect filamentous actin present in activated platelets. The coverslips were then imaged using standard fluorescence microscopy techniques. Platelets pre-activated with 20 mM ADP, a standard technique for activating platelets, adhered in similar numbers and states of spreading on all the tested surfaces, except 25% AEDAPS, to which preactivated platelets adhered poorly. In contrast, when unactivated platelets were incubated with polyelectrolyte-coated coverslips, significant differences were detected in the number that became activated and attached. Approximately the same number of platelets adhered to Nafion, a negatively charged hydrophobic surface and PAH, a positively charged hydrophilic surface, whether the platelets were pre-activated or not. Fewer pre-activated platelets adhered to surfaces of PAA and a 90:10 mol % copolymer mixture of PAA:AEDAPS than to the PAH and Nafion surfaces. Moreover, fewer unactivated than pre-activated platelets adhered to PAA surface and 90:10 PAA: AEDAPS. The most dramatic difference was observed for the 75:25 mol % copolymer mixture of PAA:AEDAPS, which had only sparsely attached platelets when incubated with unactivated platelets relative to the other surfaces (FIG. 9E). The PAA, 90:10 mol % PAA:AEDAPS and 75:25 mol % PAA:AEDAPS surfaces we have developed are resistant to platelet adherence/activation, with the 75:25 mol % PAA: AEDAPS, being particularly effective.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

The invention claimed is:

1. A method for controlling the attachment and growth of cells on a surface of an article, the method comprising contacting the article with living tissue, living organisms, or with water in an aqueous system comprising living organisms wherein the article comprises a substratum having a surface and a film on the surface, the film comprising a network of a net positively charged composition and a net negatively charged composition, wherein the net positively charged composition comprises a net positively charged polyelectrolyte or the net negatively charged composition comprises a net negatively charged polyelectrolyte, a net positively charged polyelectrolyte or the net negatively charged polyelectrolyte contains (i) a polymer repeat unit having at least two fluorine atoms, or (ii) a polymer repeat unit having a zwitterion group, and the film comprises a surface region at which a net positively charged polyelectrolyte having zwitterion repeat units, a net negatively charged polyelectrolyte having zwitterion repeat units, a net positively charged polyelectrolyte comprising a repeat unit having at least two fluorine atoms, or a net negatively charged polyelectrolyte comprising a repeat unit having at least two fluorine atoms is exposed.

2. The method of claim 1 wherein the substratum is selected from the group consisting of stents, catheters, vascular grafts, vascular prostheses, contact lenses, intraocular implants, artificial valves for in vivo use, artificial organs, dental implants, metal implants into bone, corneal implants, Petri dishes, roller bottles, microcarriers, porous structural supports for three dimensional cell growth, synthetic elastomeric polymers, and metal objects adapted for use in aqueous systems containing living organisms.

3. The method of claim 1 wherein the film is deposited by alternately layering the net positively charged composition and the net negatively charged composition and wherein layers 0 through n of the film comprise polyelectrolyte comprising non-fluorinated polymer repeat units and layers n+1 through n+2 of the film comprise polyelectrolyte comprising the polymer repeat unit having at least two fluorine atoms.

4. The method of claim 3 wherein the film promotes the attachment and growth of cells on the surface of the substratum.

5. The method of claim 1 wherein the film comprises a first surface region and a second surface region with a net positively charged or net negatively charged polyelectrolyte exposed at each of said first surface region and second surface region, wherein (1) the net positively charged or net negatively charged polyelectrolyte exposed in said first surface region contains polyelectrolyte comprising non-fluorinated polymer repeat units and (2) the net positively charged or net negatively charged polyelectrolyte exposed in said second surface region contains polyelectrolyte comprising the polymer repeat unit having at least two fluorine atoms.

6. The method of claim 5 wherein the film promotes the attachment and growth of cells on the surface of the substratum.

7. The method of claim 1 wherein the film is deposited by alternately layering the net positively charged composition and the net negatively charged composition and wherein layers 0 through n of the film comprise polyelectrolyte comprising non-zwitterion polymer repeat units and layers n+1 through n+2 of the film comprise polyelectrolyte comprising polymer repeat unit having a zwitterion group.

8. The method of claim 7 wherein the film inhibits the attachment and growth of cells on the surface of the substratum.

9. The method of claim 1 wherein the film comprises a first surface region and a second surface region with a net positively charged or net negatively charged polyelectrolyte exposed at each of said first surface region and second surface region, wherein (1) the net positively charged or net negatively charged polyelectrolyte exposed in said first surface region contains polyelectrolyte comprising non-zwitterion polymer repeat units and (2) the net positively charged or net negatively charged polyelectrolyte exposed in said second surface region contains polyelectrolyte comprising the polymer repeat unit having a zwitterion group.

10. The method of claims 9 wherein the film inhibits the attachment and growth of cells on the surface of the substratum.

11. The method of claim 1 wherein:
the net positively charged composition is a net positively charged polyelectrolyte polymer;
the net negatively charged composition is a net negatively charged polyelectrolyte polymer;
the film comprises a bulk region comprising the net positively charged polyelectrolyte polymer and the net negatively charged polyelectrolyte polymer in an interpenetrating network;
the film further comprises a first surface region and a second surface region with the net positively charged polyelectrolyte polymer or net negatively charged polyelectrolyte polymer exposed at each of said first surface region and second surface region;
the net positively charged polyelectrolyte polymer or the net negatively charged polyelectrolyte polymer exposed in said first surface region contains the polymer repeat unit having at least two fluorine atoms; and
the net positively charged polyelectrolyte polymer or the net negatively charged polyelectrolyte polymer exposed in said second surface region contains the polymer repeat unit having a zwitterion group and a charged polymer repeat unit that is non-zwitterionic.

12. A method as set forth in claim 1 wherein a positively charged polyelectrolyte or a negatively charged polyelectrolyte exposed at said surface region comprises a repeat unit having a zwitterion group.

13. A method as set forth in claim 12 wherein said positively charged electrolyte or negatively charged polyelectrolyte exposed at said surface region comprises a repeat unit having a zwitterion group and a repeat unit that is non-zwitterionic.

14. A method as set forth in claim 13 wherein said positively charged electrolyte or negatively charged electrolyte exposed at said surface region contains between 20 mole % and about 70 mole % of the repeating units that have a zwitterion group.

15. A method as set forth in claim 1 wherein a positively charged polyelectrolyte or a negatively charged polyelectrolyte exposed at said surface region comprises a repeat unit having at least two fluorine atoms.

16. A method as set forth in claim 1 wherein the article has the structure obtained by a process wherein depositing the film comprises alternately layering the net positively charged composition and the net negatively charged composition and wherein layers 0 through n of the film comprise a polyelectrolyte comprising non-fluorinated polymer repeat units and layers n+1 through n+2 of the film comprise a polyelectrolyte comprising the polymer repeat unit having at least two fluorine atoms.

17. A method as set forth in claim 1 wherein the article has the structure obtained by a process wherein depositing the film comprises alternately layering the net positively charged composition and the net negatively charged composition and wherein layers 0 through n of the film comprise a polyelectrolyte comprising non-zwitterion polymer repeat units and layers n+1 through n+2 of the film comprise a polyelectrolyte comprising polymer repeat unit having a zwitterion group.

* * * * *